(12) United States Patent
Liu et al.

(10) Patent No.: US 9,522,935 B2
(45) Date of Patent: Dec. 20, 2016

(54) COMMANDS AND METHOD OF TREATING CANCER VIA RHO PATHWAY

(71) Applicants: Xin Liu, Guangzhou (CN); Weidong Xie, Winnipeg (CA)

(72) Inventors: Xin Liu, Guangzhou (CN); Weidong Xie, Winnipeg (CA)

( * ) Notice: Subject to any disclaimer, the term of this patent is extended or adjusted under 35 U.S.C. 154(b) by 0 days.

(21) Appl. No.: 14/764,177

(22) PCT Filed: Jan. 27, 2014

(86) PCT No.: PCT/CN2014/071556
§ 371 (c)(1),
(2) Date: Jul. 29, 2015

(87) PCT Pub. No.: WO2014/117710
PCT Pub. Date: Aug. 7, 2014

(65) Prior Publication Data
US 2016/0009756 A1  Jan. 14, 2016

Related U.S. Application Data

(60) Provisional application No. 61/759,533, filed on Feb. 1, 2013.

(51) Int. Cl.
*A61K 31/336* (2006.01)
*C07D 303/06* (2006.01)
(Continued)

(52) U.S. Cl.
CPC ............ *C07J 71/001* (2013.01); *A61K 31/336* (2013.01); *C07D 303/06* (2013.01); *C07J 9/00* (2013.01);
(Continued)

(58) Field of Classification Search
CPC ............ C07J 71/001; C07J 9/00; C07J 9/005; C07J 51/00; A61K 31/336; C07D 303/06
(Continued)

(56) References Cited

PUBLICATIONS

Male et al, Analytical Methods (2010), pp. 870-877.*
Wang et al, J. Natural Products (1995), pp. 1222-1227.*
Tuck et al, J. Lipid Research (1991), pp. 893-902.*

* cited by examiner

*Primary Examiner* — Kamal Saeed
*Assistant Examiner* — Janet L Coppins
(74) *Attorney, Agent, or Firm* — Bei & Ocean; George G. Wang

(57) ABSTRACT

Lanosterol derivatives useful as anti-cancer agent, which can inhibit the growth of lung cancer cells, liver cancer cells, mammary cancer cells, brain cancer cells and pancreatic cancer cells, possibly by acting on the RHO pathway. These lanosterol derivatives are represented by compound LD030:

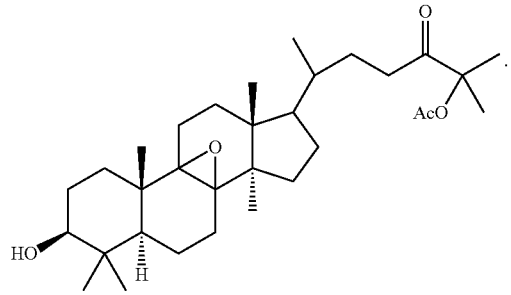

2 Claims, 15 Drawing Sheets

(51) Int. Cl.
*C07J 71/00* (2006.01)
*G01N 33/50* (2006.01)
*C07J 9/00* (2006.01)
*C07J 51/00* (2006.01)

(52) U.S. Cl.
CPC .............. *C07J 9/005* (2013.01); *C07J 51/00* (2013.01); *G01N 33/5011* (2013.01)

(58) Field of Classification Search
USPC .................................................. 514/63, 475
See application file for complete search history.

COMMANDS AND METHOD OF TREATING CANCER VIA RHO PATHWAY

CROSS-REFERENCE TO RELATED APPLICATION

This application claims benefit from U.S. provisional application No. 61/759,533, filed Feb. 1, 2013, the content of which is incorporated herein by reference in its entirety.

FIELD OF THE INVENTION

This invention relates to a method of cancer treatment via the RHO pathway. Particularly, it relates to novel lanosterol derivative compounds that have effects on the RHO pathway and are useful in treating cancers.

BACKGROUND OF THE INVENTION

Cancer is an uncontrolled growth of abnormal cells in various parts of the body. Presently cancer may be treated by surgery, radiotherapy, chemotherapy, immunotherapy, etc, with varying degrees of success. However, surgical therapy cannot completely remove extensively transferred tumor cells. Radiotherapy and chemotherapy do not have sufficient selectivity to kill cancer cells in the presence of rapidly proliferating normal cells. Immunotherapy is largely limited to the use of cytokines or therapeutic cancer vaccines. Cytokines may cause serious toxicity and continuous use of vaccines may lead to immune tolerance.

Therefore, there is need for exploring alternative routes of treatment.

Rho/Rho kinase signaling pathway is an ubiquitous signaling pathway in human body. By functioning as a signal converter or a molecular switch in cellular signal transduction pathways, it acts on the cytoskeleton or the target protein, thereby inducing actin cytoskeleton rearrangement and regulating gene transcription and cell cycle. However, there is no known method or agent that treats cancer via regulating the Rho/Rho kinase signal pathway.

SUMMARY OF THE INVENTION

Accordingly, one object of the present invention is to provide a new group of compounds which possess anticancer effects via a novel mechanism. This object is achieved by providing the compounds of the following formulas, which have anticancer activities via regulating the Rho/Rho kinase signal pathway:

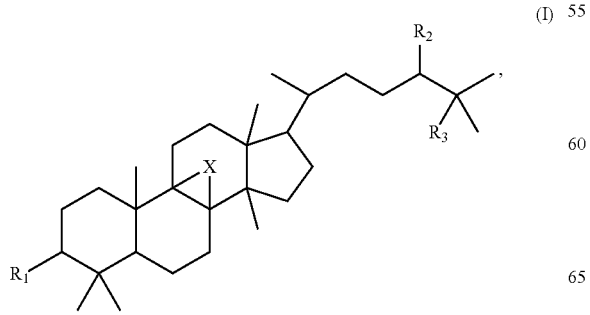
(I)

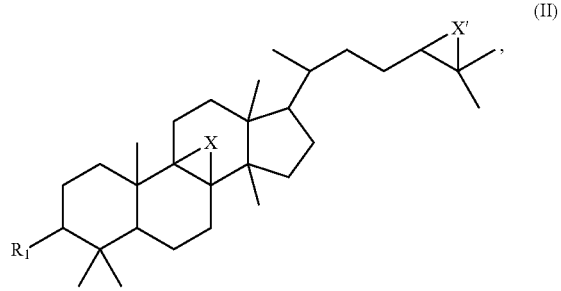
(II)

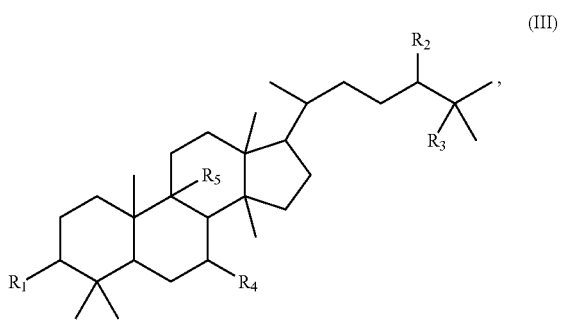
(III)

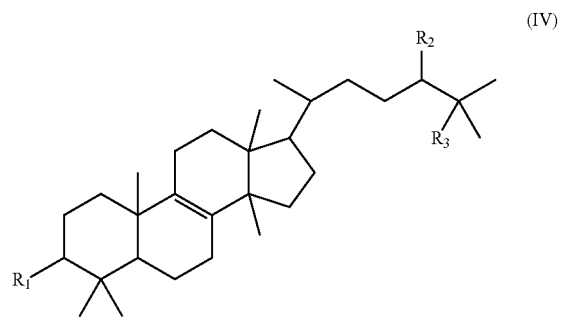
(IV)

wherein X, X' is O, S or NR; R1 and R2 are independently hydrogen, halogen, —OH, —SH, =O, C1-C5 alkyl group, C1-C5 alkoxy group, p-methyl phenylsulfonyl, alkane-substituted siloxy or C1-C5 alkylamino; R3, R4, and R5 are independently hydrogen, halogen, —OH, —SH, C1-C5 alkyl group, C1-C5 alkoxy group, methylphenylsulfonyl group, a silyl group, or C1-C5 alkyl amino; R is alkyl or hydrogen.

The preferred compounds of formula (I) are as follows:

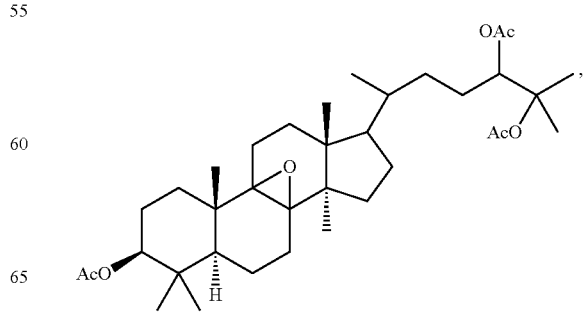

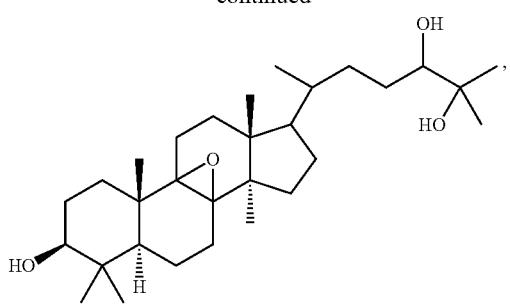
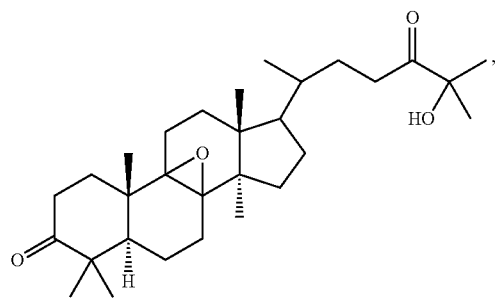
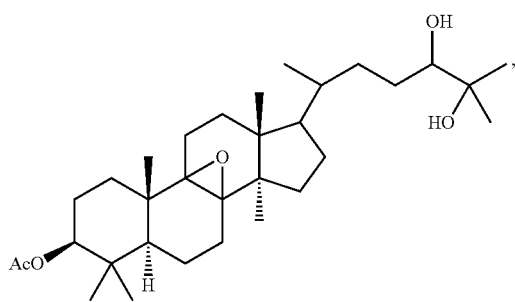
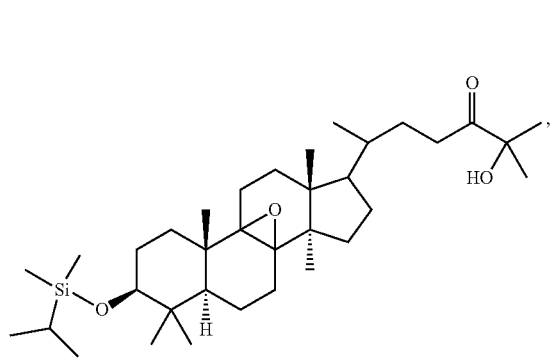
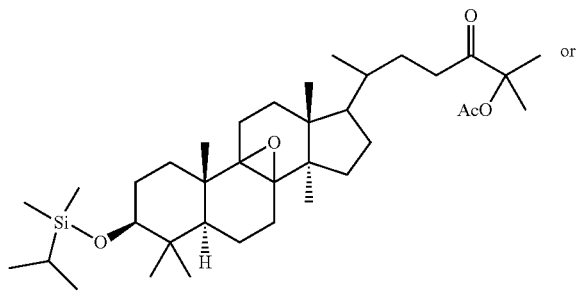
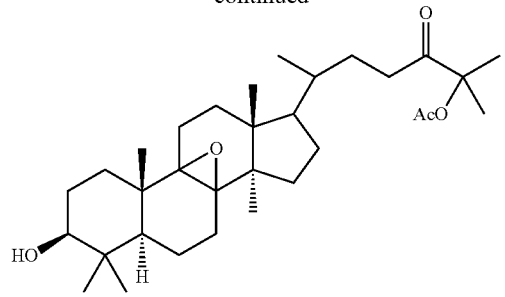
The preferred compounds of formula (II) are:
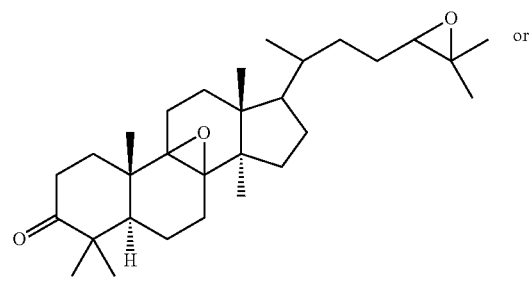
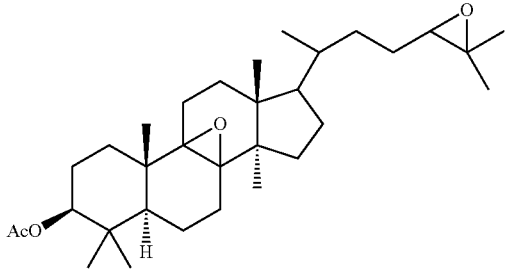
The preferred compounds of formula (III) is:
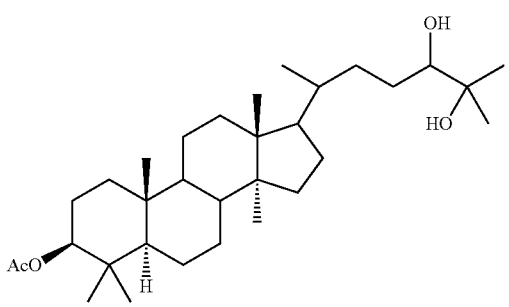 [SMILES: CC(=O)O[C@H]1CC[C@]2(C)C3CC[C@]4(C)C(C(C)CCC(O)C(C)(C)O)CC[C@@]4(C)C3CC[C@H]2C1(C)C]
The preferred compounds of formula (IV) are:
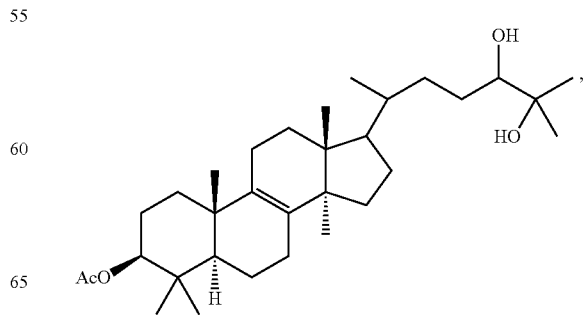

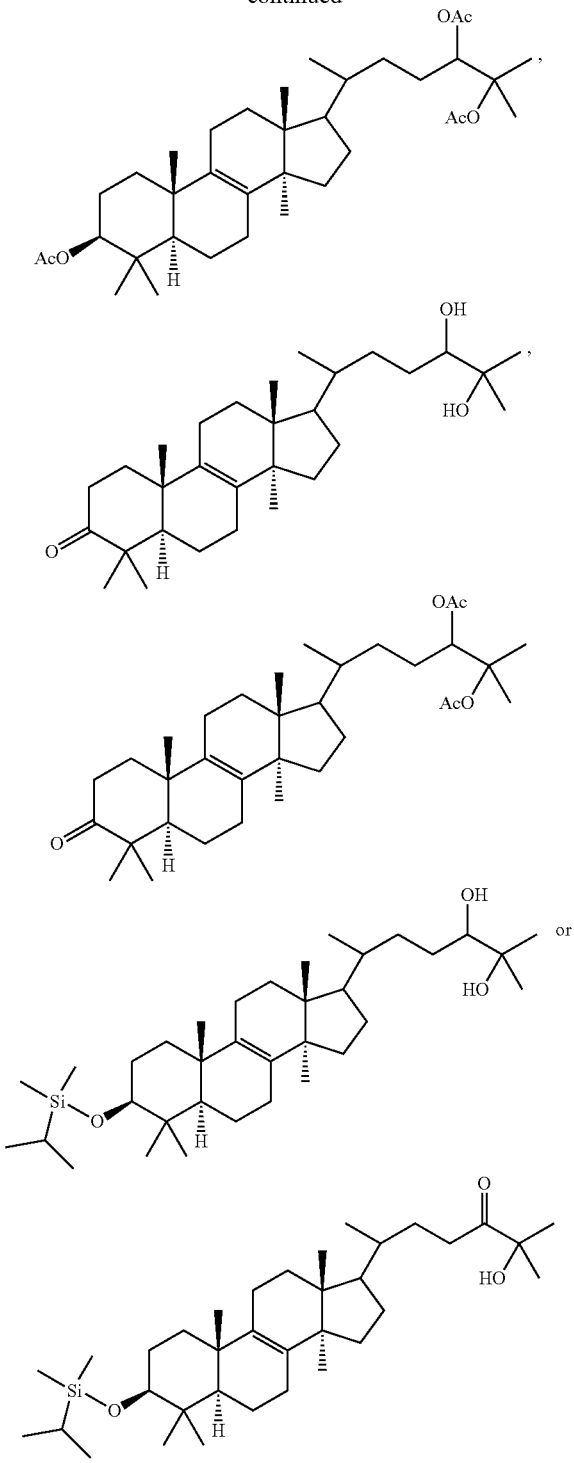

Another object of the present invention is the use of the above compounds in the preparation of anti-cancer drugs. Preferably, the drug contains gemcitabine or Nexavar in combination with one or more of the above compounds.

Compared with the existing anticancer agents, the beneficial effects of the present invention are as follows:

(1) The compounds of the present invention features a novel targeting site and very low toxic side effect. Animal experimental data demonstrated that the representative compound LD030 is a potent agent in inhibiting a variety of solid tumors, such as liver cancer and pancreatic cancer. The target site of LD030 appears to be Rac-1, which is a phosphokinase of Rho signaling channel. Binding of LD030 to Rac-1 interferes the Rac-1's role in regulating protein expression of JAK2/STAT3, and thus inhibits the tumor growth.

(2) The compounds of the present invention have a different anti-tumor mechanism from existing drugs and can inhibit growth of hepatocellular carcinoma through three routes: inhibition of tumor cell proliferation, inhibition of tumor angiogenesis, and induction of cancer cell apoptosis. Animal experiments show that compound LD030 has little toxicity at the cellular and animal level.

(3) Experiments showed that the compounds of this invention can selectively inhibit the growth of cancer cells, while having little effect on the normal cells.

(4) The compounds of this invention can be used alone or in combination with other drugs, especially with gemcitabine or Nexavar.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DISCRETION OF THE INVENTION

Figure 1:
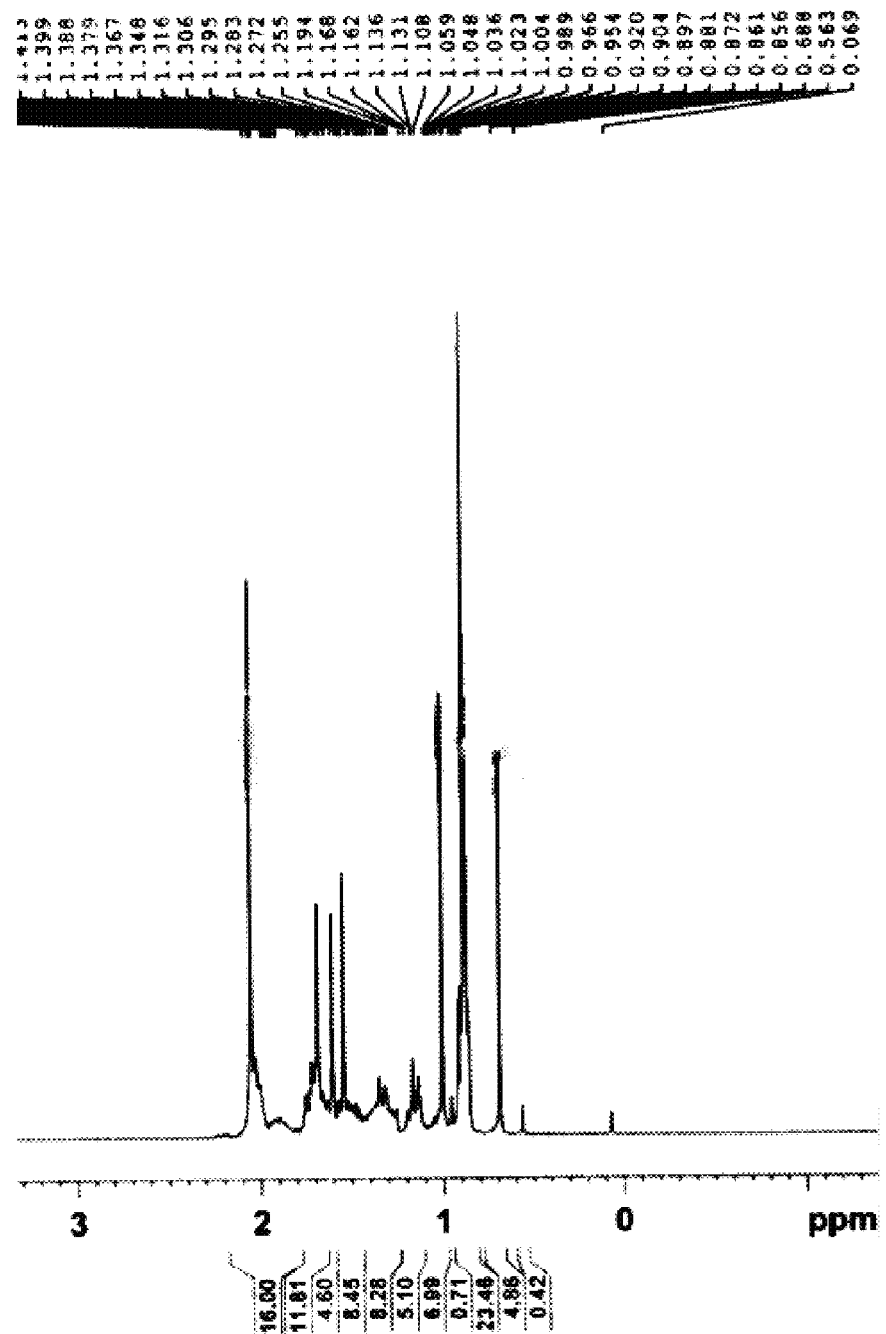
FIG. 1 shows $^1$H NMS spectrum of LD020 (CDCL3 as solvent).

Synthesis of Lanosterol Derivatives (1) 5 g lanosterol was dissolved in 20 ml pyridine, and after lanosterol being completely dissolved, added 2 ml acetic anhydride (approximately 2 equivalents). The mixture was reacted at room temperature for 12 hours. The reaction mixture was then concentrated under a reduced pressure, cooled in ice bath, and slowly added with 10% sodium bicarbonate aqueous solution (mass concentration) till there was no air bubble emerging. The mixture was extracted with ethyl acetate for three times and the organic layers were combined. After washing with saturated sodium chloride, the organic layer was dried over anhydrous sodium sulfate for ten to thirty minutes. After filtration, the organic layer was spun and dried to get ~5.5 g crude product, which yielded 4.5 g white solid target product (referred to as ID20) after going through column separation. The yield was about 84%. MS (ESI): m/z 569 [M+H$^+$]. The spectrum is shown in FIG. 1: $^1$HNMR (CDCl3, 400 MHz), 4.51 (1H, m), 2.08 (3H, s, Me). The reaction equation is:

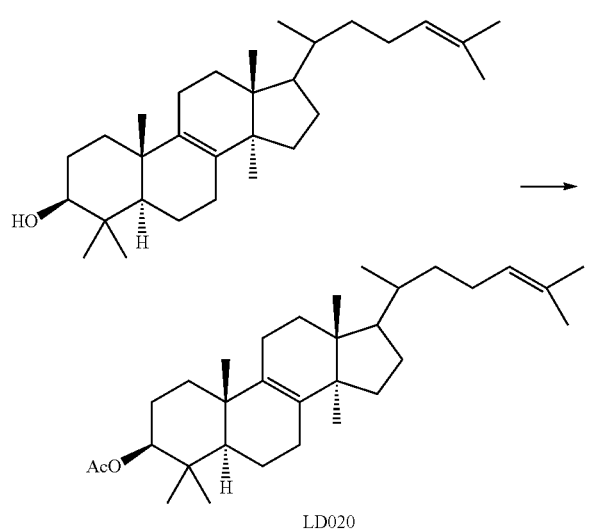

Figure 2:
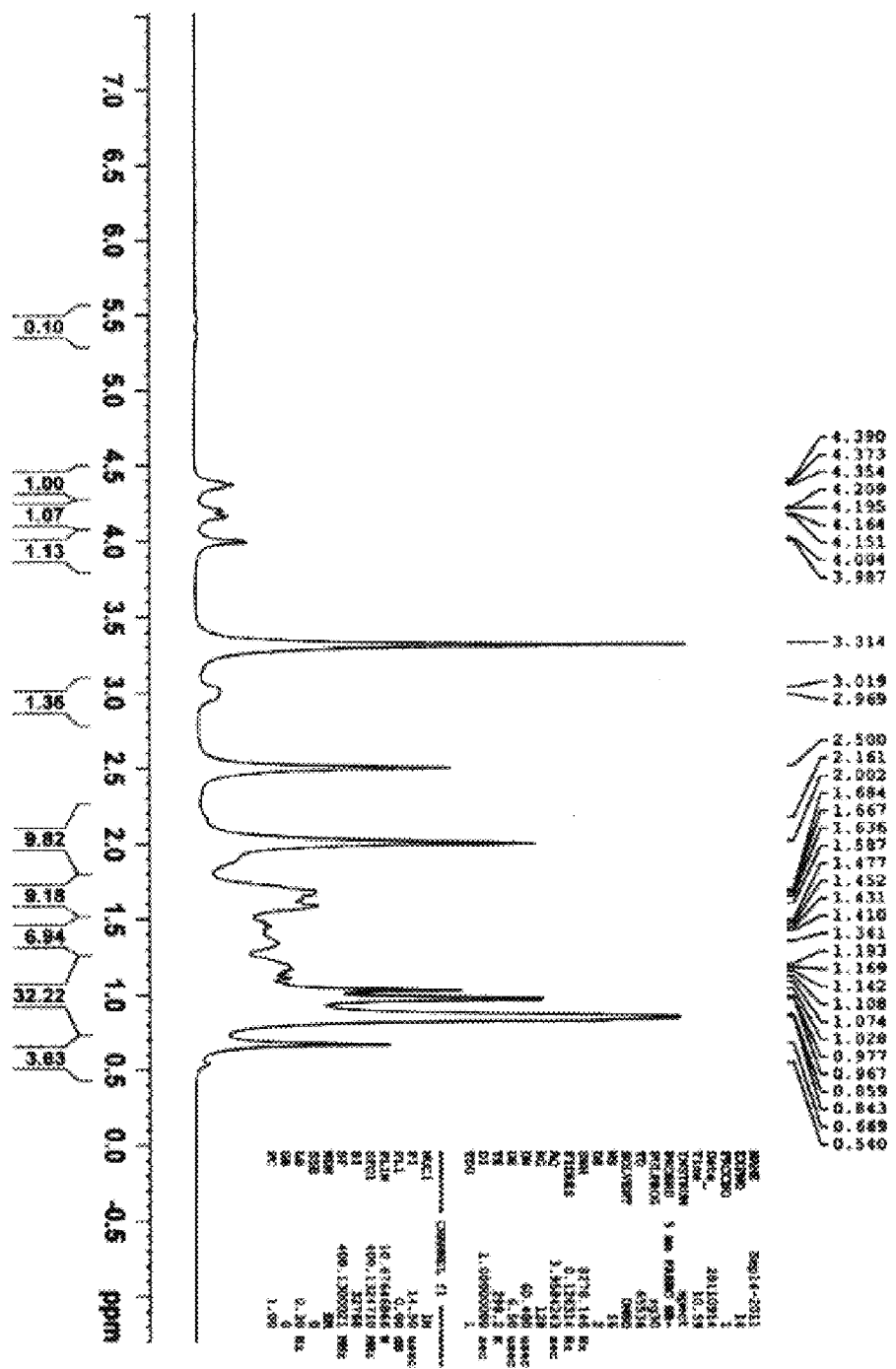
FIG. 2 shows $^1$H NMR spectrum of LD021 (DMSO as solvent).

(2) 4 g LD020 was dissolved in 40 ml acetone, and slowly added with 0.02 g (the catalytic amount) osmium tetroxide and 3 g (3 equivalents) N-oxide-N-methyl-morpholine (NMO) under vigorous stirring. Continue stirring the mixture at room temperature for 7 days to complete the reaction. The reaction mixture was concentrated under reduced pressure and the residue was added with about 30 ml of saturated sodium chloride solution and extracted with dichloromethane (50 ml each) for three times. The dichloromethane layers were combined and washed with saturated sodium chloride solution, dried over anhydrous sodium sulfate. After filtration, the organic layer was spun and dried to get about 2.8 g crude product, which yielded 1.6 g white solid target product (referred to as LD021) after going through column separation. The yield was about 40%. MS (ESI): m/z 503 [M+H$^+$]. The NMR spectrum is shown in FIG. 2: $^1$HNMR (DMSO, 400 MHz), 4.35 (1H, m), 4.15 (1H, m), 3.99 (1H, m), 2.08 (3H, s, Me). The reaction equation is:

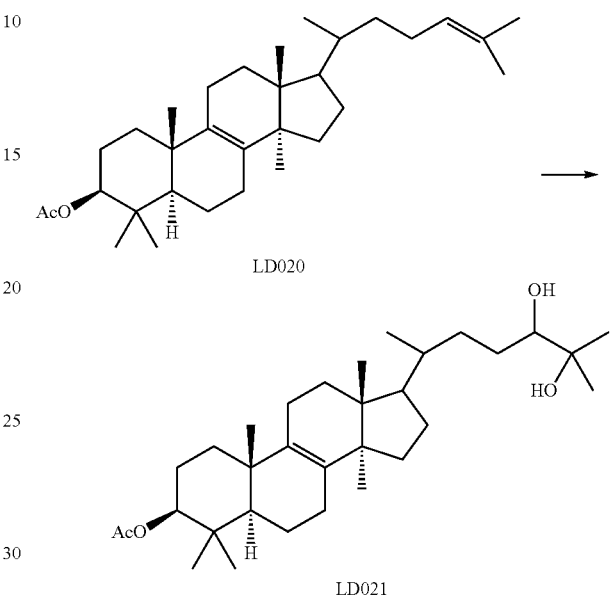

(3) 1.5 g LD021 was dissolved in 10 ml pyridine, and upon completely dissolved, added with 1.4 ml acetic anhydride (about 5 equivalents). The mixture was reacted at room temperature for 12 hours. The reaction mixture was concentrated under reduced pressure, then cooled in ice bath, and slowly added with 10% sodium bicarbonate aqueous solution (mass concentration) until there were not bubbles emerging. Extract the mixture with ethyl acetate for three times and combine the organic layers. After being washed with saturated sodium chloride, the organic layer was dried over anhydrous sodium sulfate for ten to thirty minutes. After filtration, the organic layer was spun and dried to get about 2 g crude product which yielded 1.5 g of white solid target product (referred to as LD022) after going through column separation. The yield was about 88%. MS (ESI): m/z 587[M+H$^+$]; $^1$HNMR (DMSO, 400 MHz), 4.35 (1H, m), 4.15 (1H, m), 3.99 (1H, m), 2.00 (9H, s, 3Me). The reaction equation is:

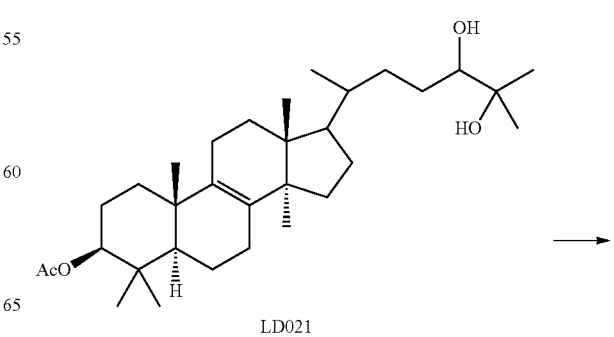

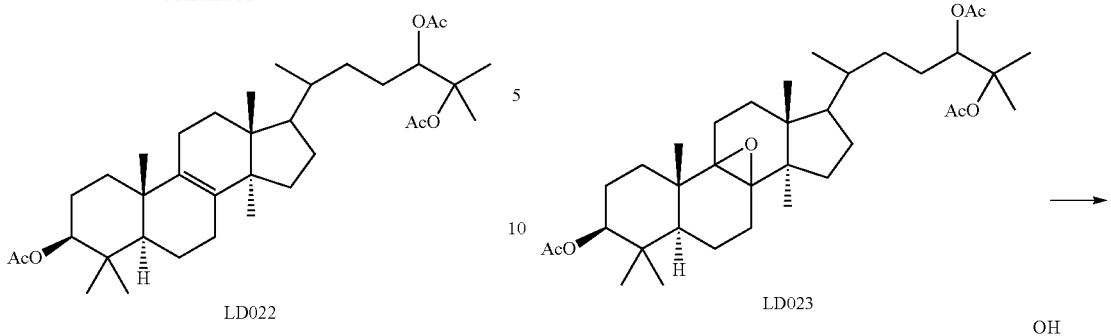

(4) 1.4 g LD022 was dissolved in 40 ml dichloromethane and then added with 0.6 g of m-chloroperbenzoic acid (MCPBA, about 1.5 equivalents) under vigorous stirring. After stirring for 10 hours at 0° C., 1 g of calcium hydroxide was added and stirring was continued at room temperature for 1 hour. The mixture was filtered to get rid of the solid, which was washed with methylene chloride (about 50 ml). After filtration, the organic layer was spun and dried to get about 0.8 g white solid target product (referred to as LD023) after going through column separation. The yield was about 55%. MS (ESI): m/z 603 [M+H$^+$]; $^1$HNMR (DMSO, to 400 MHz), 4.37 (1H, m), 4.15 (1H, m), 3.99 (1H, m), 2.00 (9H, s, 3Me). The reaction equation is:

(5) 0.7 g LD023 was dissolved in 10 ml potassium carbonate saturated aqueous, and the reaction was continued for 2 hours under stirring at room temperature. After concentrating the reaction mixture under reduced pressure, the solid was dissolved and washed with dichloromethane for three times (each time 50 ml) and the dichloromethane layers were combined, and then spun and dried to get about 0.35 g white solid target product (referred to as LD024) after going through column separation. The yield is about 75%. MS (ESI): m/z 477 [M+H$^+$]. The reaction equation is:

(6) 0.3 g (0.6 mmoles) LD024 was dissolved in 50 ml dichloromethane with continuous stirring, and 0.4 g pyridinium chlorochromate (PCC, approximately 3 equivalents) was added. After the reaction was stirred at room temperature for 2 hours, 50 ml anhydrous ether was added. Separate the ether layer and washed the black residue with ether for 3 times (each time with 50 ml of diethyl ether). The ether layers were combined and 0.15 g white solid target product (referred to as LD025) was obtained after going through silica gel separation. The yield was 51%. MS (ESI): m/z 473 [M+H$^+$]. The reaction equation is:

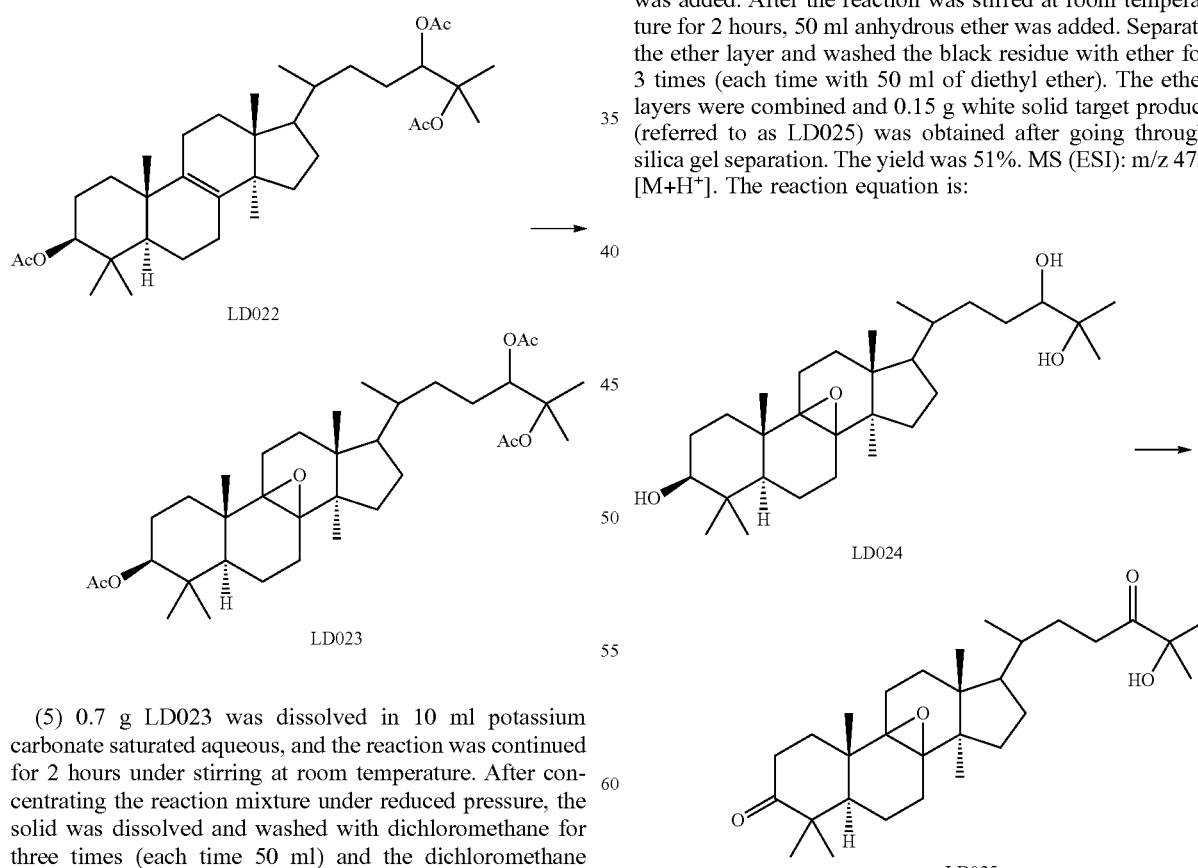

(7) 0.1 g LD020 was dissolved in 10 ml dichloromethane, and added with 0.08 g m-chloroperbenzoic acid (MCPBA, about 3 equivalents) under vigorous stirring. After stirring for 10 hours at 0° C., 0.1 g of calcium hydroxide was added and stirring was continued at room temperature for 1 hour. Filtration was conducted to get rid of the solid, which was further washed with methylene chloride (about 50 ml). All the liquid portions were combined and concentrated to obtain crude product, which was going through column separation to yield about 20 mg white solid product 1 and 30 mg white solid product 2, referred to as LD026-1 and LD026-2, respectively. The yield is separately about 18% (LD026-1) and 28% (LD026-2). LD026-1: MS (ESI): m/z 485[M+H$^+$], LD026-2: MS (ESI): m/z 501[M+H$^+$]. The reaction equation is:

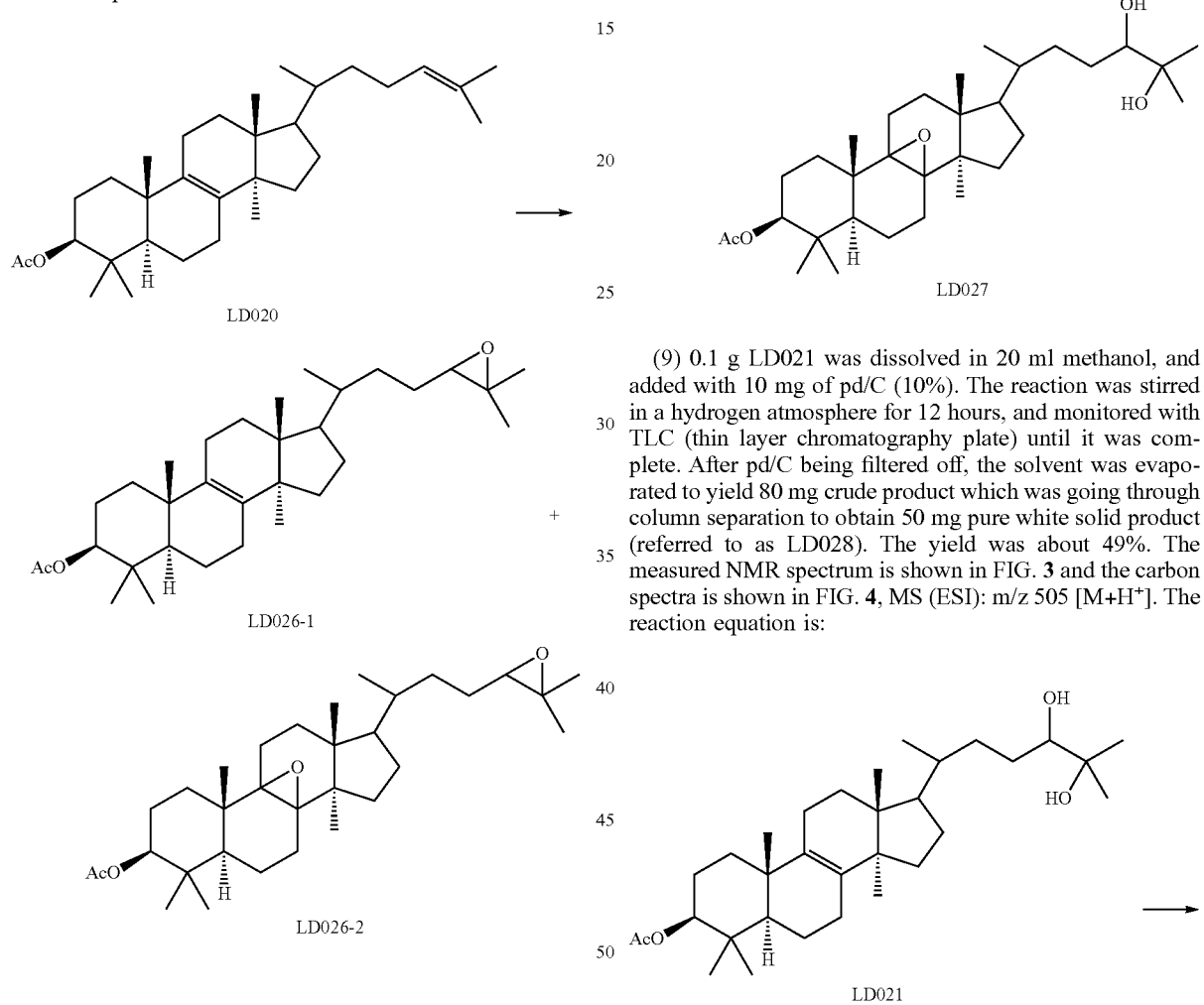

(8) 0.1 g LD021 was dissolved in 10 ml dichloromethane, and then added with 0.04 g m-chloroperbenzoic acid (MCPBA, about 1.5 equivalents) under vigorous stirring. After stirring for 10 hours at 0° C., 0.1 g of calcium hydroxide was added and stirring was continued at room temperature for 1 hour. Filtration was conducted to remove the solid which was further washed with methylene chloride (about 50 ml). The liquid portions were combined and concentrated to get about 10 mg white solid product (referred to as LD027) after going through column separation. The yield was about 10%. $^1$HNMR (DMSO, 400 MHz), 4.35 (1H, m), 4.15 (1H, m), 3.99 (1H, m), 2.08 (3H, s, Me). MS (ESI): m/z 519[M+H$^+$]. The reaction equation is:

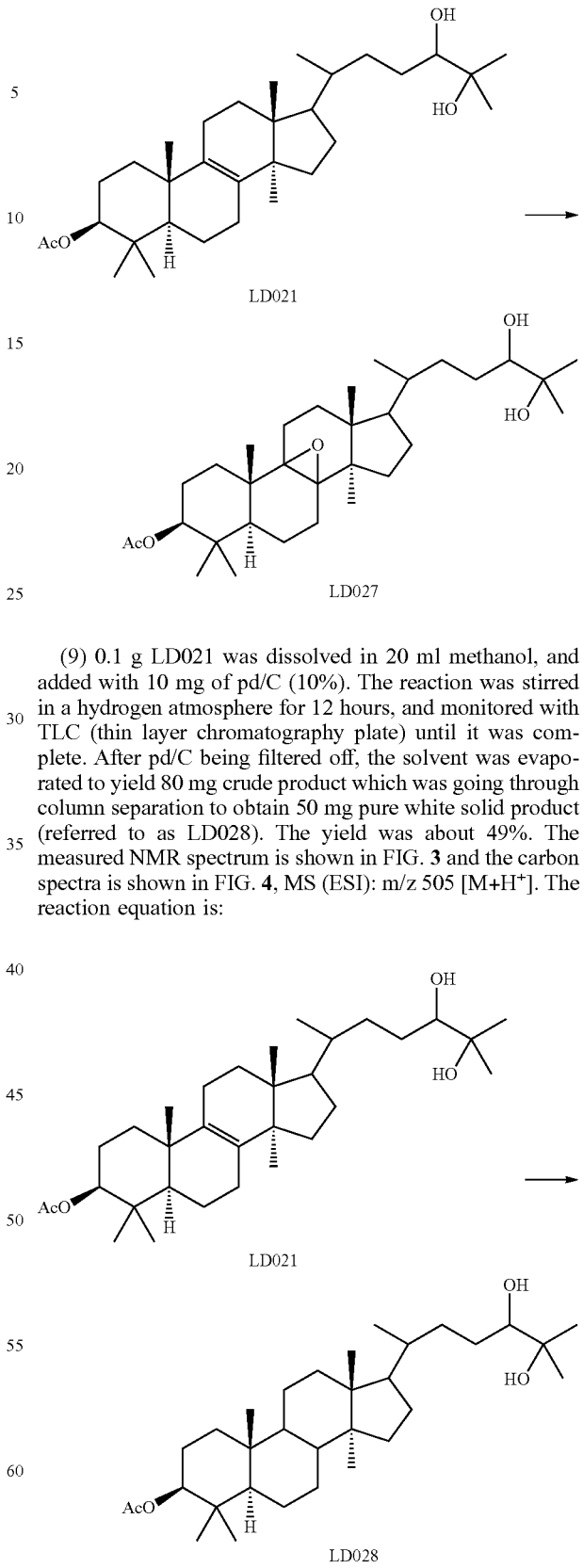

Figure 3:
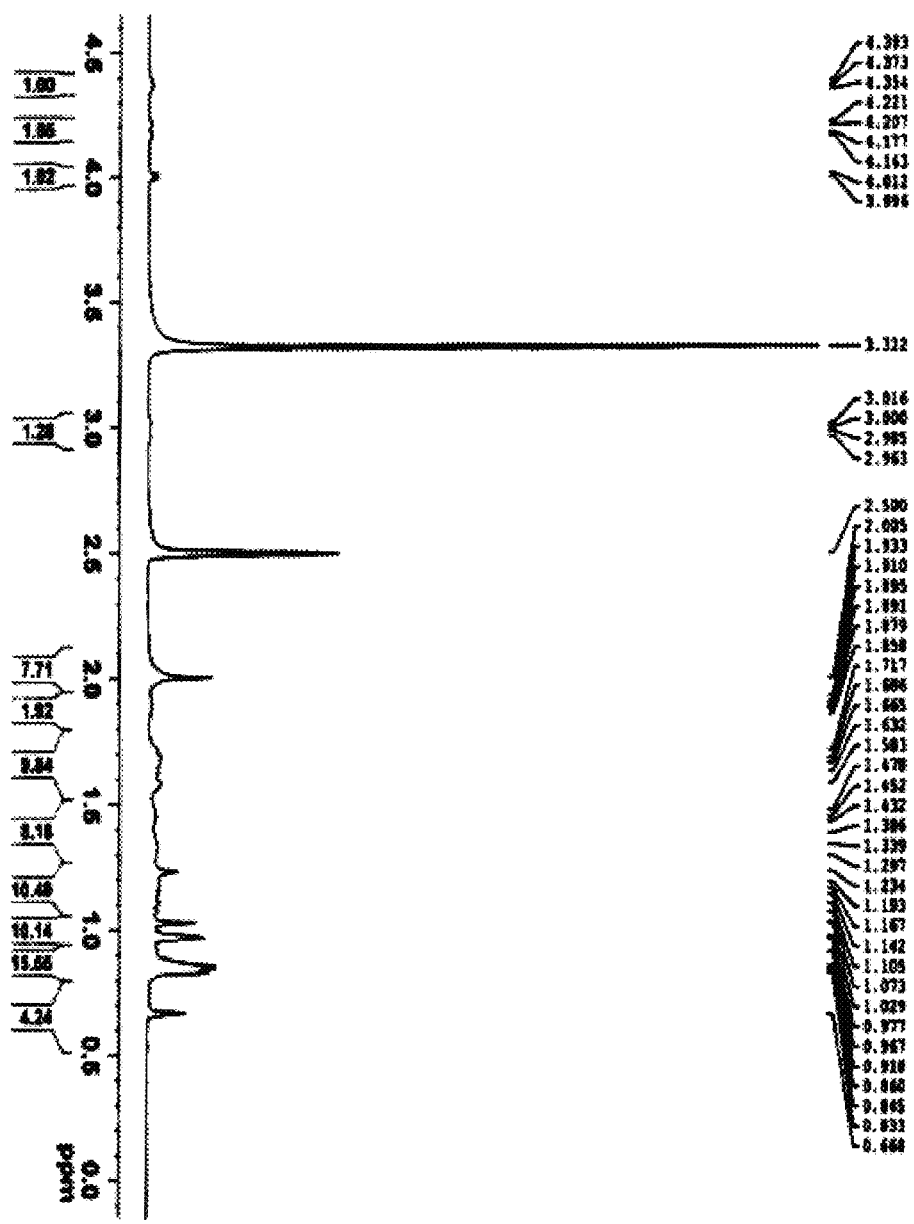
FIG. 3 shows $^1$H NMR spectrum of LD028 (DMSO as solvent).
Figure 4:
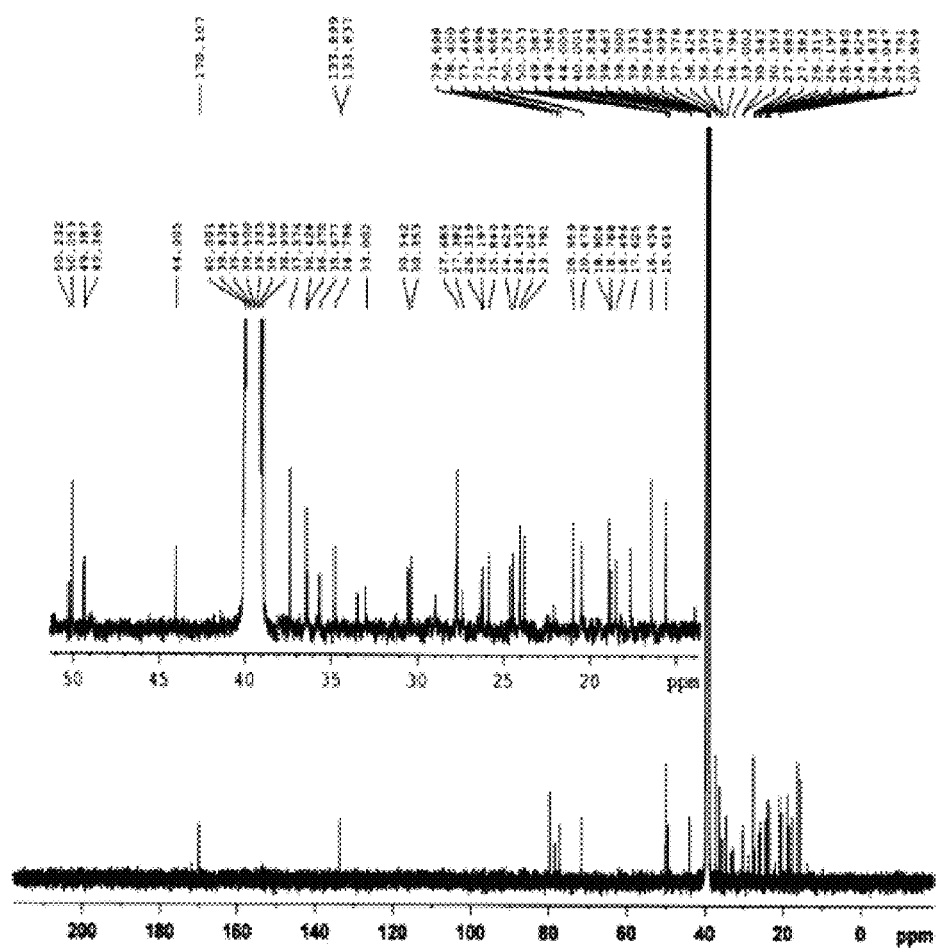
FIG. 4 shows $^{13}$C NMR spectrum of LD028 (DMSO as solvent).

(9) 0.1 g LD021 was dissolved in 20 ml methanol, and added with 10 mg of pd/C (10%). The reaction was stirred in a hydrogen atmosphere for 12 hours, and monitored with TLC (thin layer chromatography plate) until it was complete. After pd/C being filtered off, the solvent was evaporated to yield 80 mg crude product which was going through column separation to obtain 50 mg pure white solid product (referred to as LD028). The yield was about 49%. The measured NMR spectrum is shown in FIG. 3 and the carbon spectra is shown in FIG. 4, MS (ESI): m/z 505 [M+H$^+$]. The reaction equation is:

(10) 1 g (2.3 mmoles) lanosterol was dissolved in 50 ml dichloromethane under constant stirring, and then added with 1 g pyridinium chlorochromate (PCC, approximately 1.6 equivalents). The reaction was stirred at room temperature for 2 hours before adding 50 ml anhydrous ether. The ether layer was separated from the black residue which was washed with ether for 3 times (each time with 50 ml of diethyl ether). then ether portions were combined and going through silica gel separation to yield 0.45 g the white solid product (referred to as LD012). The yield was 45%. MS (ESI): m/z 425[M+H$^+$]. The reaction equation is:

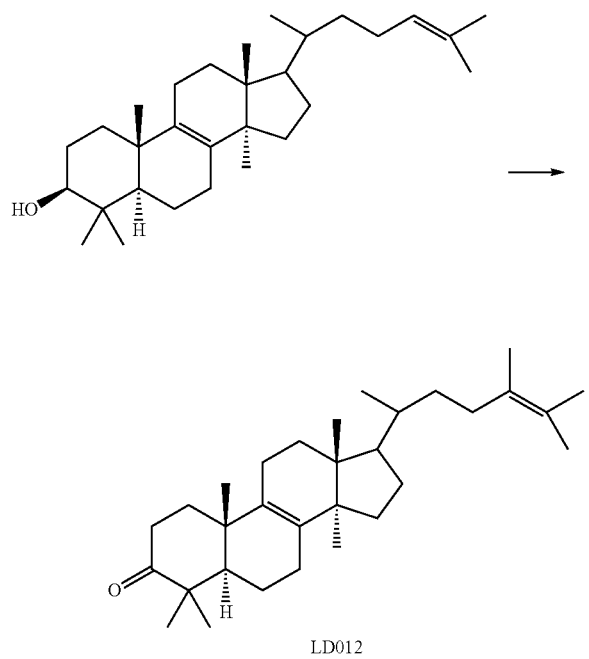

LD012

(11) 0.1 g LD012 was dissolved in 10 ml dichloromethane, and then added with 0.08 g m-chloroperbenzoic acid (MCPBA, about 3 equivalents) under vigorous stirring. After stirring for 10 hours at 0° C., 0.1 g of calcium hydroxide was added and stirring was continued at room temperature for 1 hour. Filtration was conducted to remove the solid which was further washed with methylene chloride (about 50 ml). The liquid portions were combined and concentrated to get a crude product which yield about 41 mg white solid product (referred to as LD015) after going through column separation. The yield was about 40%. The reaction equation is:

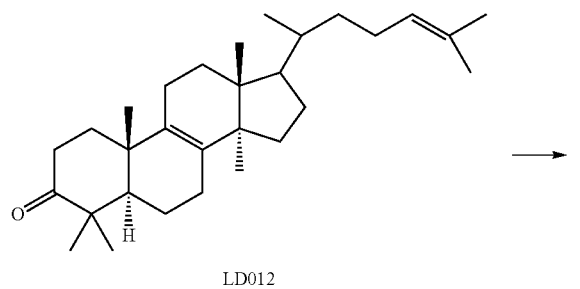

LD012

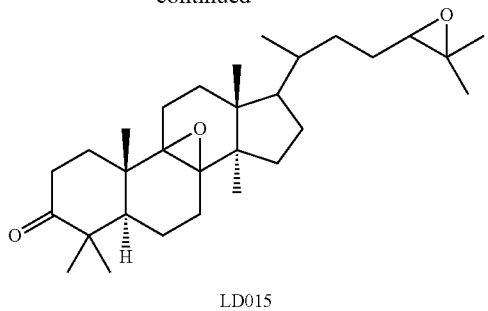

LD015

(12) 0.2 g LD012 was dissolved in 40 ml acetone, and slowly added with 0.01 g (catalytic amount) osmium tetroxide and 0.15 g (3 equivalents) N-oxide-N-methyl-morpholine (NMO) under vigorous stirring. The reaction mixture was under constant stirring at room temperature for 7 days before the reaction was terminated. The reaction mixture was then concentrated under reduced pressure, and the residue was added with about 30 ml of saturated sodium chloride solution and extracted with dichloromethane for three times (50 ml each time). The dichloromethane layers were combined and washed with saturated sodium chloride solution. It was then dried over anhydrous sodium sulfate. After removing the solvent, a crude product was obtained which yielded 1.6 g the white solid product (referred to as LD013) after going through column separation. The yield was about 20%. MS (ESI): m/z 459[M+H$^+$]. The reaction equation is:

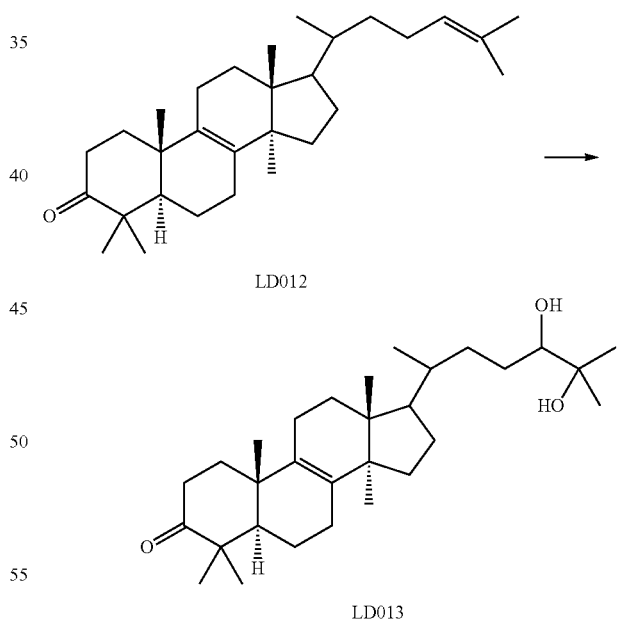

(13) 20 mg LD013 was dissolved in 4 ml pyridine, and added with 0.1 ml acetic anhydride (about 5 equivalents). The mixture was then reacted at room temperature for 12 hours. The reaction mixture was concentrated under reduced pressure, and then cooled the mixture with ice bath and slowly added 10% sodium bicarbonate aqueous solution (mass concentration) till there were no bubbles emerging. The mixture was extracted with ethyl acetate for three times and the organic layers were combined. After washing with saturated sodium chloride, the combined organic layer was dried over anhydrous sodium sulfate for ten to thirty minutes. After filtration, the organic layer was spun and dried to get crude product, which yielded 15 mg white solid product (referred to as LD014) after going through column separation. The yield was about 60%. MS (ESI): m/z 543 [M+H$^+$]. The reaction equation is:

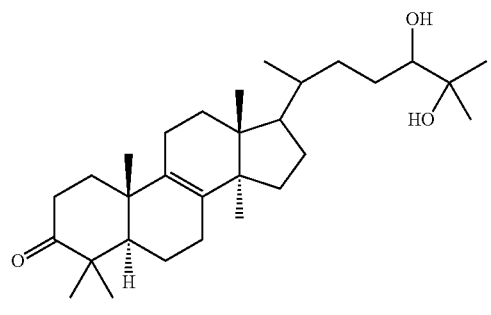

(14) 5 g lanosterol was dissolved in 50 ml DMF, and added with 3.7 ml (about 2 equivalents) (DMIPS.HCl) and 1 ml imidazole. The mixture was stirred for ten hours at room temperature and then concentrated under reduced pressure. The concentrated mixture was slowly added with 10% sodium bicarbonate aqueous solution (mass concentration) till there were no bubbles emerging, and then extracted with ethyl acetate for three times. The organic layers were combined. After washing with saturated sodium chloride, the organic layer was dried over anhydrous sodium sulfate for ten to thirty minute. Then, it was filtered, spun and dried to get crude product, which yielded 5 g white solid product (referred to as LD031) after going through column separation. The yield was about 80%. MS (ESI): m/z 527[M+H$^+$]. The reaction equation is:

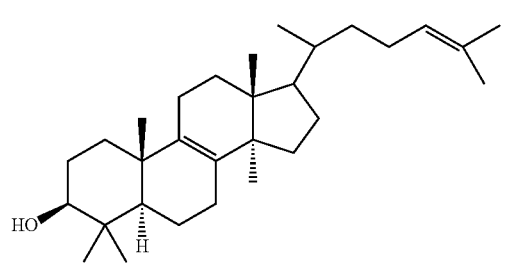

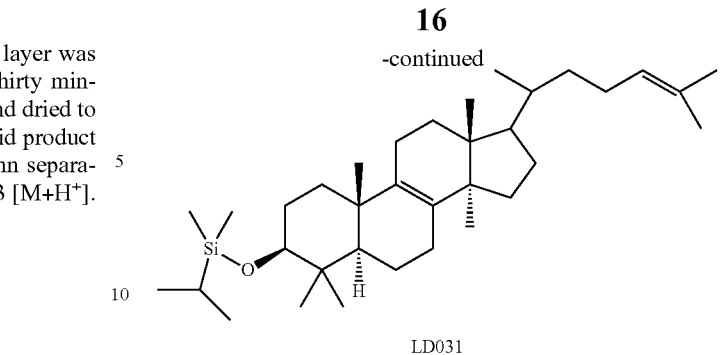

(15) 0.2 g LD031 was dissolved in 40 ml acetone, and slowly added with 0.01 g (in catalytic amount) osmium tetroxide and 3 g (3 equivalents) N-oxide-N-methyl-morpholine (NMO) under vigorous stirring. The reaction continued under stirring at room temperature for 7 days. The reaction mixture was concentrated under reduced pressure and then added about 50 ml of saturated sodium chloride solution and extracted with dichloromethane (50 ml each) for three times. The dichloromethane layers combined and washed with saturated sodium chloride solution, and dried over anhydrous sodium sulfate. It was filtered, spun and dried to get 2.6 g crude product, which yielded 1.5 g the white solid product (referred to as LD032) after going through column separation. The yield was about 38%. MS (ESI): m/z 561 [M+H$^+$]. The reaction equation is:

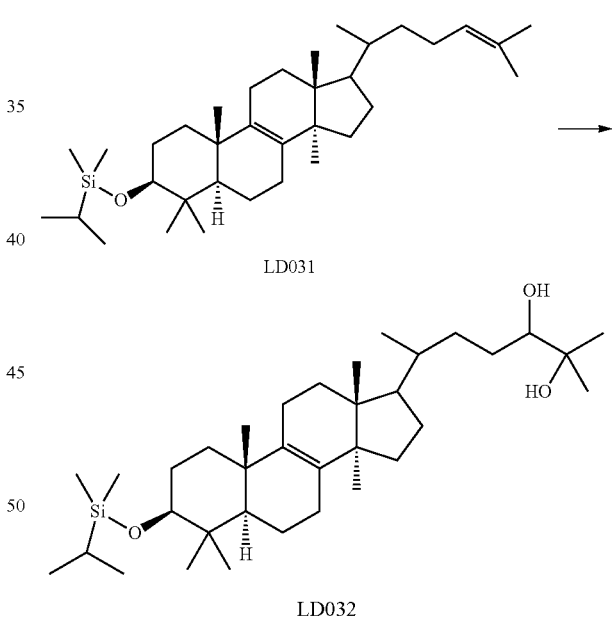

(16) 1 g (0.6 mmoles) LD032 was dissolved in 50 ml dichloromethane under constant stirring, and then added with 0.8 g pyridinium chlorochromate (PCC, approximately 3 equivalents). The reaction was stirred at room temperature for 2 hours and 50 ml anhydrous ether was added. Separate the ether layer and the solid was washed with ether for 3 times (each time with 50 ml of diethyl ether). All the ether portions were combined, which yielded 0.4 g white solid product (referred to as LD033) after going through silica gel separation. The yield was 70%. MS (ESI): m/z 559[M+H$^+$]. The reaction equation is:

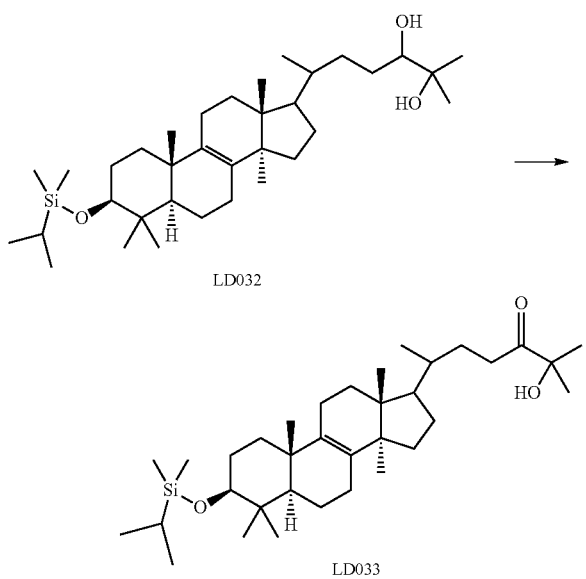

LD032

LD033

(17) 0.8 g LD033 was dissolved in 40 ml dichloromethane, and then added with 0.6 g m-chloroperbenzoic acid (MCPBA, about 1.5 equivalents) under vigorous stirring. The reaction continued under stirring for 10 hours at 0° C. Then, 1 g of calcium hydroxide was added under stirring at room temperature for 1 hour before filtering off the solid, which was further washed with methylene chloride (about 50 ml). The liquid portions were combined and concentrated to get a crude product, which yielded about 0.6 g white solid product (referred to as LD034) after going through column separation. The yield was about 65%. MS (ESI): m/z 575 [M+H$^+$]. The reaction equation is:

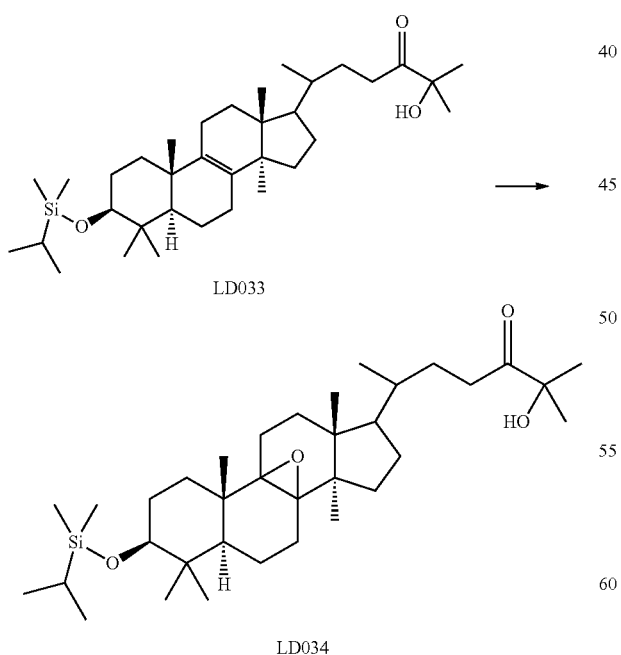

LD033

LD034

(18) 0.5 g LD034 was dissolved in 10 ml pyridine, and added with 1.4 ml acetic anhydride (about 5 equivalents). The mixture was then reacted at room temperature for 12 hours. The reaction mixture was concentrated under reduced pressure and cooled with ice bath, and then slowly added with 10% sodium bicarbonate aqueous solution (mass concentration) till there were no bubbles emerging. It was then extracted with ethyl acetate for three times. The organic layers were combined and washed with saturated sodium chloride, and then was dried over anhydrous sodium sulfate for ten to thirty minute, filtered, spun and dried to get a crude product, which yielded 0.48 g white solid product (referred to as LD035) after going through column separation. The yield was about 88%. MS (ESI): m/z 617[M+H$^+$]. The reaction equation is:

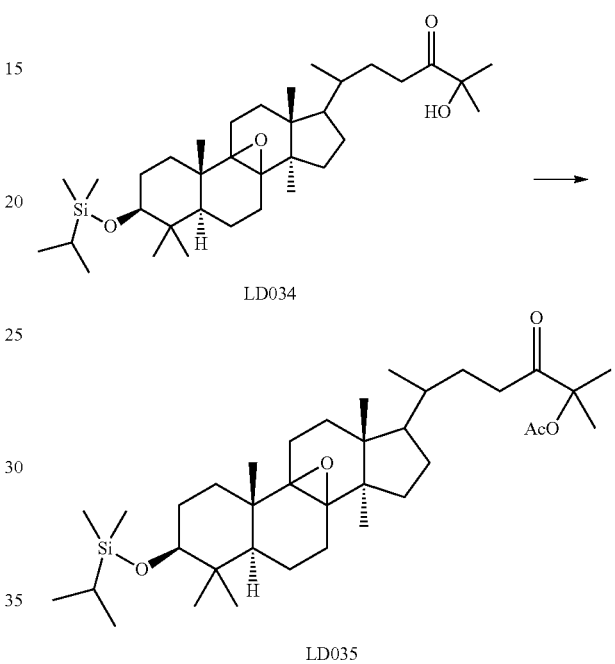

LD034

LD035

Figure 5:
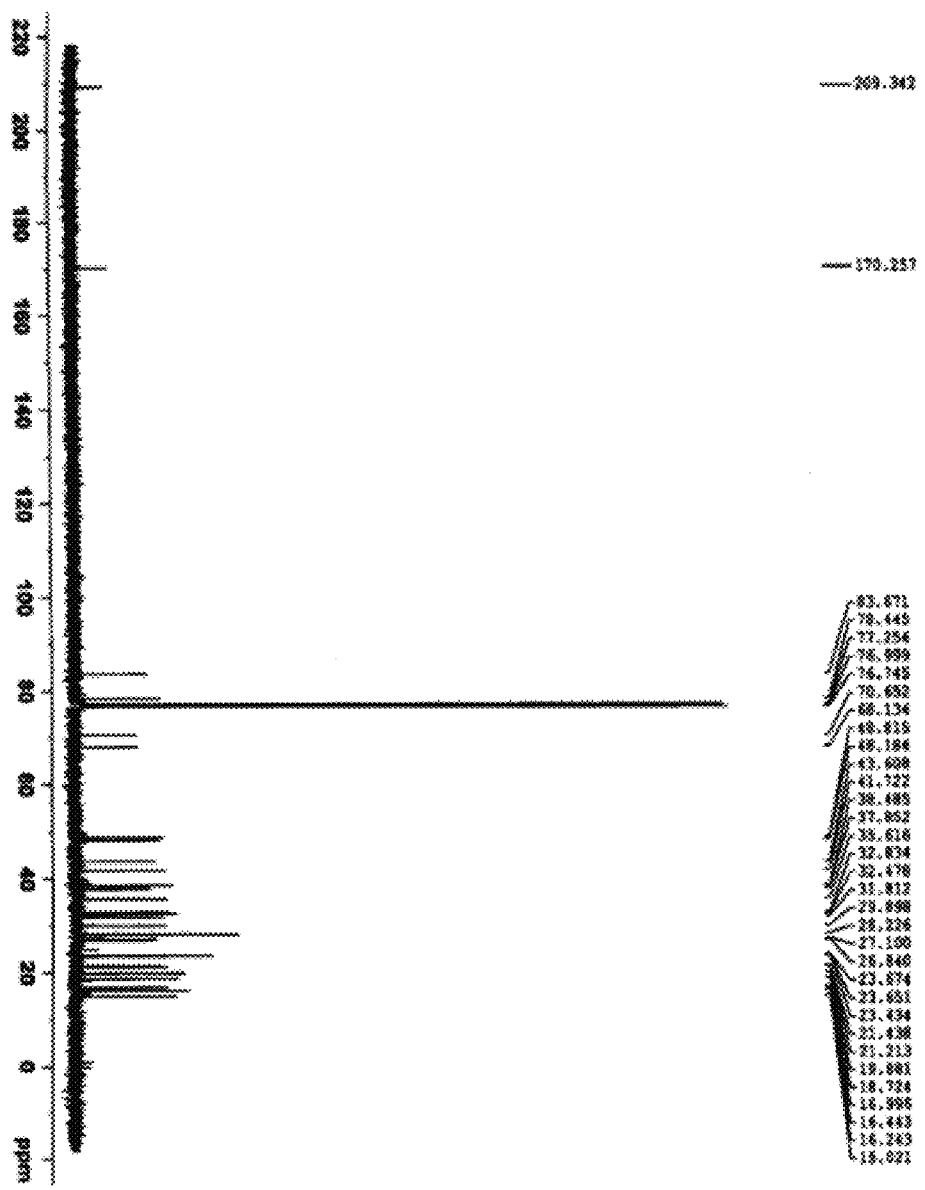
FIG. 5 shows $^{13}$C NMR spectrum of LD030 (CDCl3 as solvent).
Figure 6:
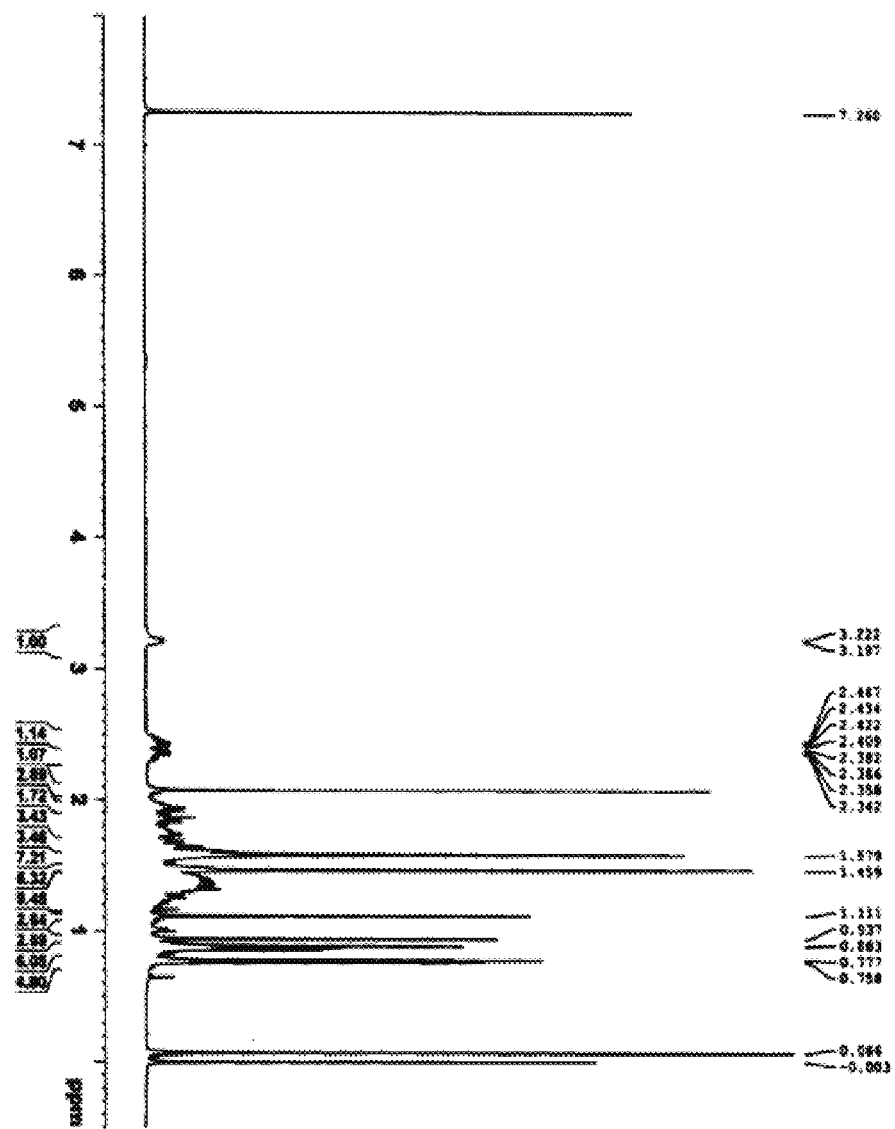
FIG. 6 shows $^1$H NMR spectrum (CDCl3 as solvent).
Figure 7:
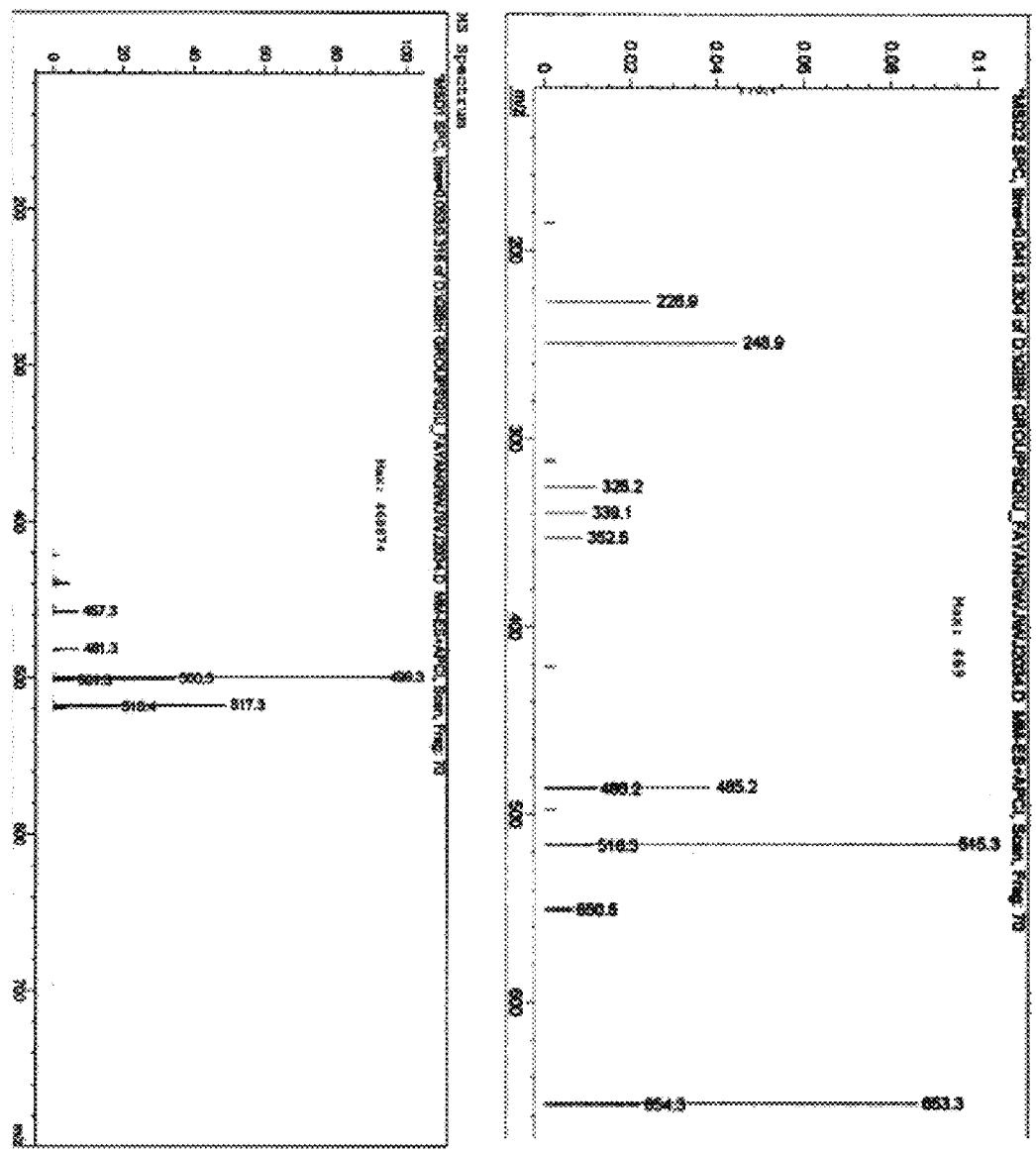
FIG. 7 shows MS spectrum of LD030.

(19) 0.3 g LD035 was dissolved in 10 ml THF, and added with 0.1 g Bu4N+F−, allowing the reaction continue under stirring at room temperature for one hour. The reaction mixture was first concentrated under reduced pressure, and then washed with DCM for 3 times (50 ml each time), the DCM solutions were combined and concentrated to get a crude product, which yield 0.15 g white solid product (referred to as LD030) after going through column separation. The yield was about 88%. $^{13}$CNMR (CDCl3, 400 MHz), 209.3, 170.3, 83.7, 78.4, 70.7, 68.1. $^1$HNMR (CDCl3, 400 MHz), 3.20 (1H, d, J=10 Hz), 2.342 (2H, m), 2.08 (3H, s, Me). MS (ESI): m/z 517[M+H$^+$]. The measured NMR spectrum is shown in FIG. 5, the carbon spectra is shown in FIG. 6, and the MS is shown in FIG. 7. The reaction equation is:

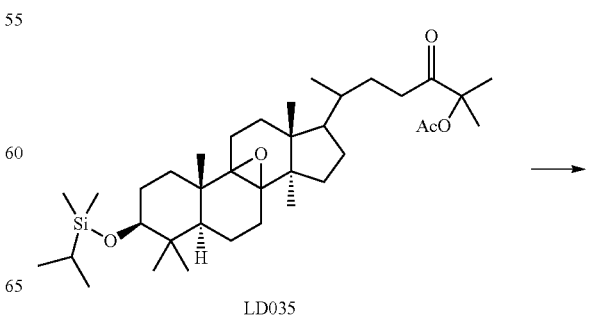

LD035

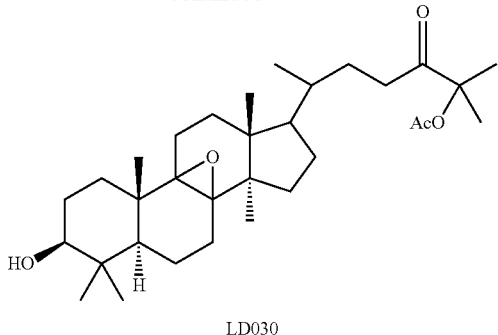

LD030

Effect of Compound LD030 on Cancer Cell Lines

Figure 12:
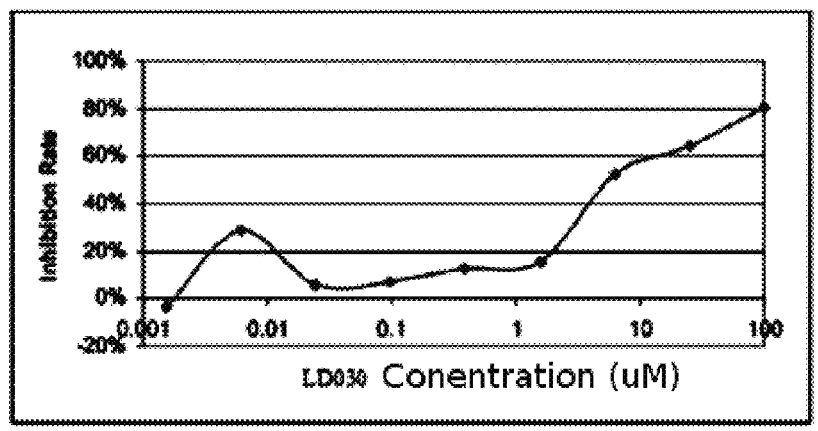
FIG. 12 shows a growth curve of NCI-H460 cells under the LD030 treatment.
Figure 13:
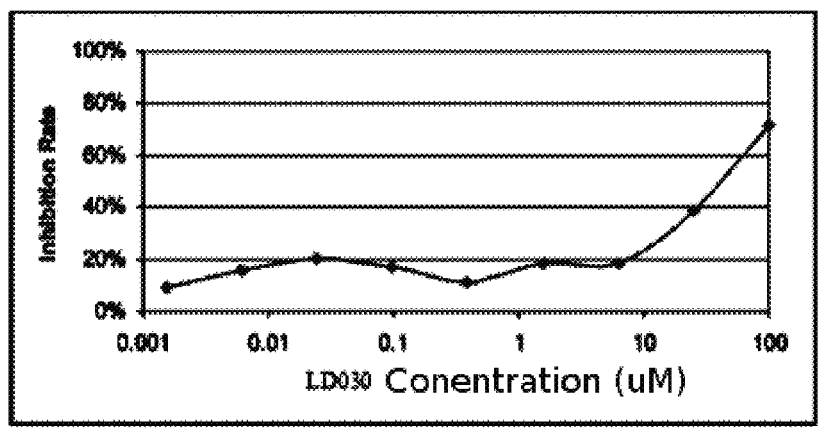
FIG. 13 shows a growth curve of MCF-7 cells under the LD030 treatment.
Figure 14:
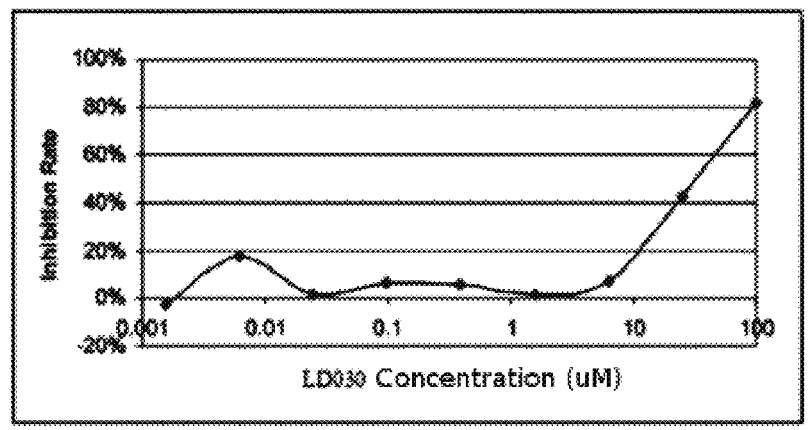
FIG. 14 shows a growth curve of SF-268 cells under the LD030 treatment.

MTT assay, a well known method known in the art, was used to analyze anticancer effects of compound LD030 on human cancer cell lines, such as, HepG2 (liver cancer cell line), PancI (pancreatic cancer cell line), NCI-H460 (lung cancer cell line), MCF-7 (breast adenocarcinoma cell line) and SF-268 (brain tumor cell lines). An LD030 solution was diluted gradually to obtain a serial of LD030 solutions with decreasing concentrations, which was used to treat various cancer cell lines mentioned above incubated in separate container. After incubation for 48 hours, the MTT agent was added to each container and the OD570 value of the formazan precipitate in each container were measured to obtain the inhibition rate on cell growth. For incubating with HepG2 cell line, LD030's concentrations were 0.001 μM, 0.01 μM, 0.1 μM, 1 μM, 10 μM, 100 μM. For PancI cell line, the concentrations were 0.1 μM, 1 μM, 10 μM, 100 μM. For NCI-H460 cell line, the concentrations were 0.001 μM, 0.01 μM, 0.1 μM, 1 μM, 10 μM, 100 μM. For MCF-7 cell line, the concentrations were 0.001 μM, 0.01 μM, 0.1 μM, 1 μM, 10 μM, 100 μM. For SF-268 cell line, the concentrations were 0.001 μM, 0.01 μM, 0.1 μM, 1 μM, 10 μM, 100 μM. The cell growth inhibition rates for HepG2, PancI, NCI-H460, MCF-7 and SF-268 are shown in FIGS. 12 to 14, respectively. The results demonstrated that, at 100 μM, LD030 show an inhibition rate above 80% on all cancer cell lines tested.

Toxicity Study of LD030 on BALB/c Mice

LD030 animal toxicity experiments were conducted in adult BALB/c mice. The mice were subject to a LD039 dosage of 1-16 mg/Kg via peritoneal injection. No significant toxicity was observed on all treated BALB/c mice and the mice were still alive after 14 days. The results confirmed that at a dosage as high as 16 mg/Kg LD030 is safe to BALB/c. By short-term toxicological experiment, the half-lethal dose LD50 (under continuous treatment) is 4 mg/kg, and the median effective dose ED50 of 0.2 mg/kg, resulting in a therapeutic Index of 20 (that is, LD50/ED50≈20).

Effects of LD030 on Proliferation of Pancreatic Cancer Cell in Nude Mouse Model

Two strains of pancreatic cancer cell lines were selected to be grafted to nonobese diabetic/severe combined immunodeficient (NOD/SCID) mice, and the tumor was inoculated in mouse ventral sides. About two weeks, they were used as a nude mouse model of pancreatic cancer.

Figure 15:
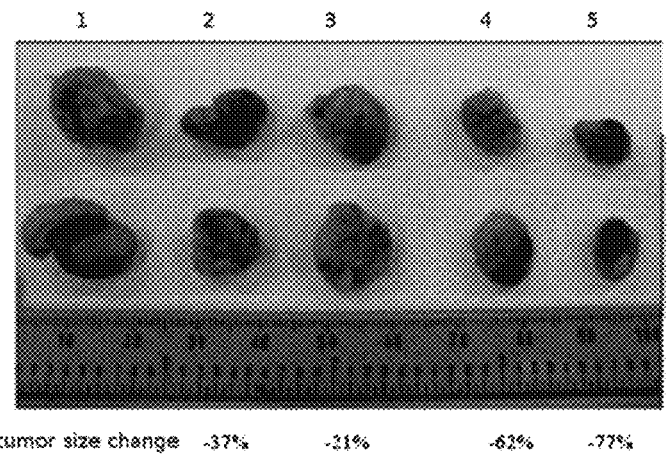
FIG. 15 shows changes in actual tumor size after treatment with LD030.

The nude mouse model was subject to five experimental treatments, which were set up as follows: (1) blank control, (2) 25 mg/kg/time gemcitabine, (3) 0.5 mg/kg/time LD030, (4) 1 mg/kg/time LD030, and (5) 0.5 mg/kg/time LD030 together with 25 mg/kg/times gemcitabine. 43 days after such treatment (3 time a week), the tumor size in the nude mice of pancreatic cancer was recorded, which were shown in FIG. 15. As shown in FIG. 15, for treatment groups 2, 3, 4, and 5, the tumor volume were reduced by 37%, 21%, 62%, and 77%, respectively. This result demonstrate that, for pancreatic cancer cells, 1 mg/kg LD030 has a better efficacy than 25 mg/kg gemcitabine, and the composition with both LD030 and gemcitabine has a better efficacy than either of the two compounds alone.

Figure 16:
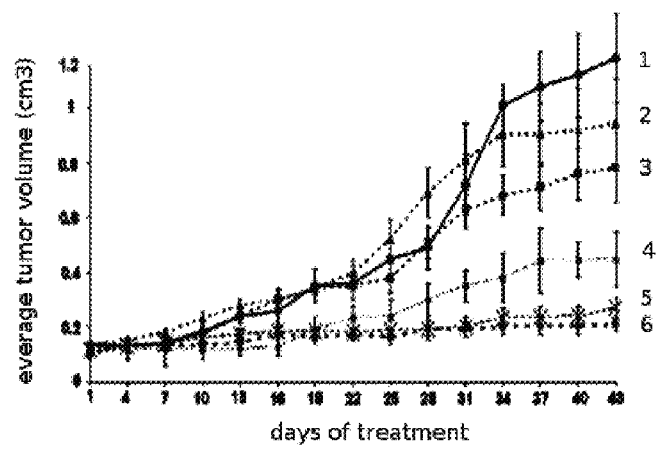
FIG. 16 shows a curve of tumor size changes after treatment with LD030.

In addition, another study was conducted with six treatment groups: (1) blank control, (2) 0.5 mg/kg/time LD030, (3) 25 mg/kg/time gemcitabine, (4) 1 mg/kg/time LD030, (5) 0.5 mg/kg/time LD030 gether with 25 mg/kg/time kat decitabine, and (6) 1 mg/kg/time LD030 together with 25 mg/kg/time gemcitabine. Each of the above groups. The treatment continued for 43 days (gemcitabine alone group 2 times a week; other groups 3 times a week), and then tumor size was recorded as shown in FIG. 16. As shown in FIG. 16, the effect of suppressing tumor size is increasing in the order from group 1 to group (6). Again, it demonstrated that combinational use of LD030 with gemcitabine is better than either compound alone.

Figure 17:
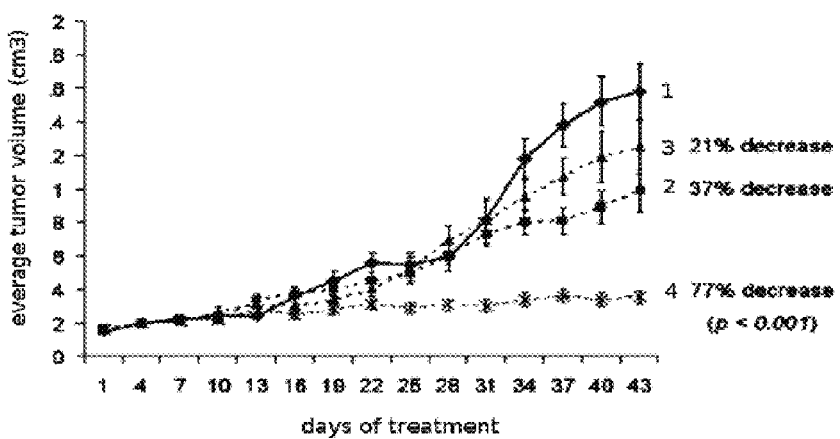
FIG. 17 shows a curve of tumor size after treatment with LD030, gemcitabine and combination of both.

Further experiments were conducted to study the effects of the combinational use of LD030 with gemcitabine as compared being used alone on tumor inhibition. Four treatment groups were set up: (a) blank control, (2) gemcitabine (25 mg/kg/time, 2 times a week), (3) LD030 (0.5 mg/kg/time, 3 times a week), (4) LD030 (0.5 mg/kg/time, 3 times a week) together with gemcitabine (25 mg/kg/time, 2 times a week). Treatment continued for 43 days and the tumor size was recorded, which is shown in FIG. 17. The result shows that, in the xenograft model, combination of LD030 with gemcitabine reduced the tumor size by 77%, while gemcitabine alone reduced by 37%, and LD030 alone by 21%. Thus, LD030 combined with gemcitabine has an enhanced inhibitory effect on the growth of pancreatic cancer.

Figure 18:
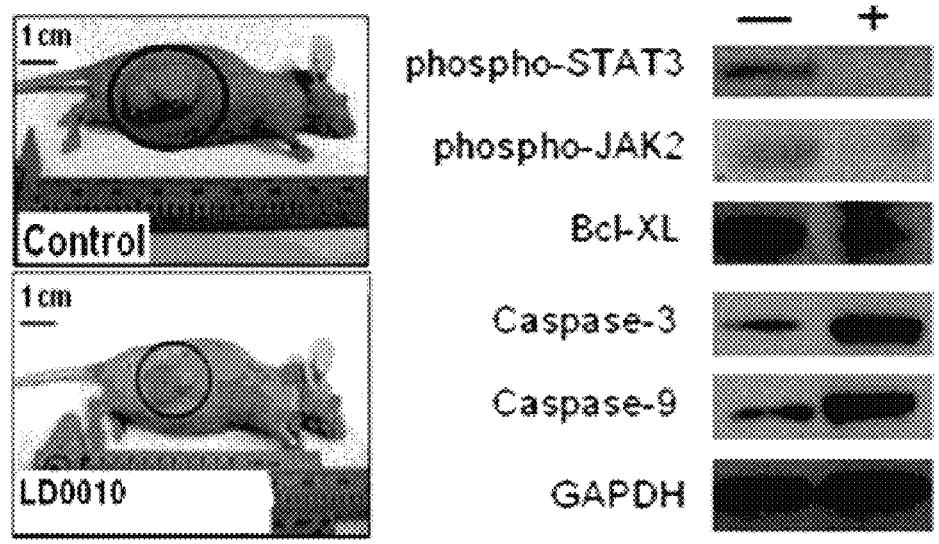
FIG. 18 shows physical tumor sizes in the left and corresponding protein electrophoresis in the right, showing changes after the LD030 treatment.

LD030's effect on the growth of allograft pancreatic cancer cell lines was further studied as follows: Each mouse model was given 0.01 mg/kg LD030 via intraperitoneal injection, three times a week. The result is shown in FIG. 18, where the left side shows the actual tumor size (compared with untreated control mouse) and indicate the tumor was significantly reduced with the treatment. Extracted from the treated mouse and the control mouse, the phosphorylation-signal transduction and activator of transcription (p-STAT3), phospho-JAK2 (p-JAK2), Bcl-XL, apoptosis protease 3, 9 and GADPH (glyceraldehyde-3-phosphate dehydrogenase, or aldehyde dehydrogenase) were subject to protein electrophoresis. The electrophoresis results are shown in the right side of FIG. 18, which indicates that, after treatment, the expression of p-STAT3, p-JAK2, and Bcl-XL significantly were significantly reduced while expression of apoptosis protease 3, 9 was significantly increased. GADPH was used as an internal reference, the expression of which was basically unchanged. Therefore, it is suggested that LD030 can down-regulate p-STAT3, p-JAK2, Bcl-XL, while up-regulating the function of caspase 3, 9.

Figure 19:
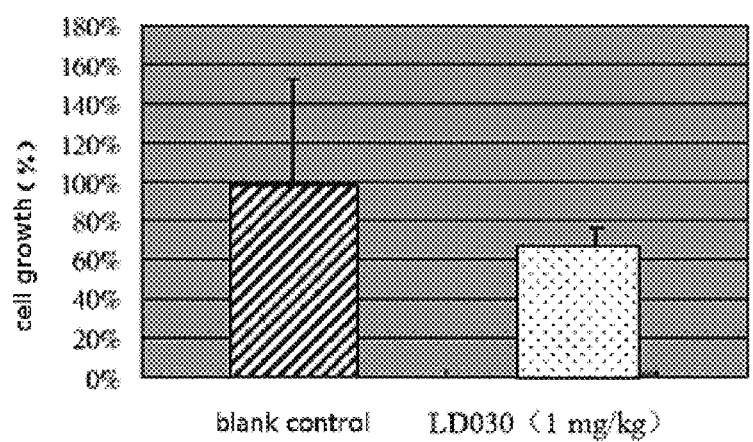
FIG. 19 shows the effect of LD030 on HepG2 cell growth.

Effects of LD030 on Proliferation of Hepatoma Cells in Nude Mouse Model of Hepatocellular Carcinoma The effect on LD030 treatment on the growth of HepG2 cells in the nude mouse model was shown in FIG. 19. The experiment used the blank carrier ethanol as control, which did not change the growth rate of the cells. In contrast, LD30 (1 mg/kg/time, twice a day) reduced the growth rate of HepG2 cells by about 63%, with statistical significance ($p<0.05$) when compared with the ethanol control.

Figure 20:
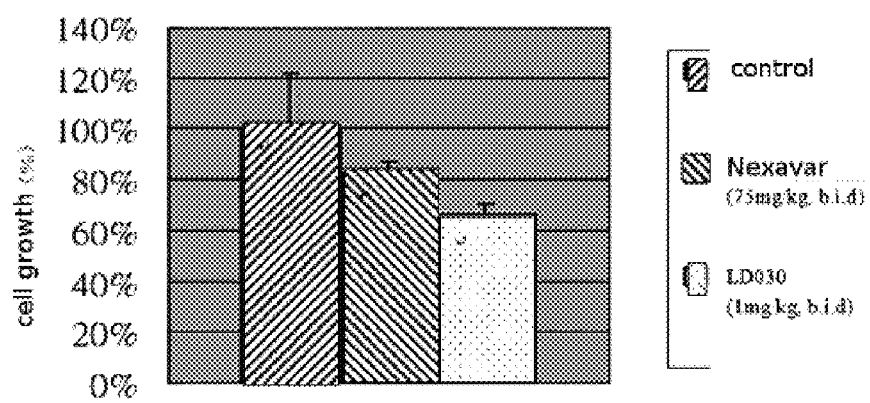
FIG. 20 shows the effect on HepG2 cell growth when treated with LD030 in combination with Nexavar in terms of percentage of untreated control.

LD030 was also compared with Nexavar for their effects on the growth rate of HepG2 cells. The result is shown in FIG. 20 and demonstrates that while the blank carrier control did not affect the the growth rate, Nexavar (75 mg/kg, twice a day) reduced the growth rate by about 80% and LD030 (1 mg/kg, twice a day) reduced it by about 63%. Thus, LD030 has the effect of inhibiting the hepatoma cell lines and the effect is statistically significant (p<0.05), although, at lower dosages, Nexavar is more effective.

Figure 21:
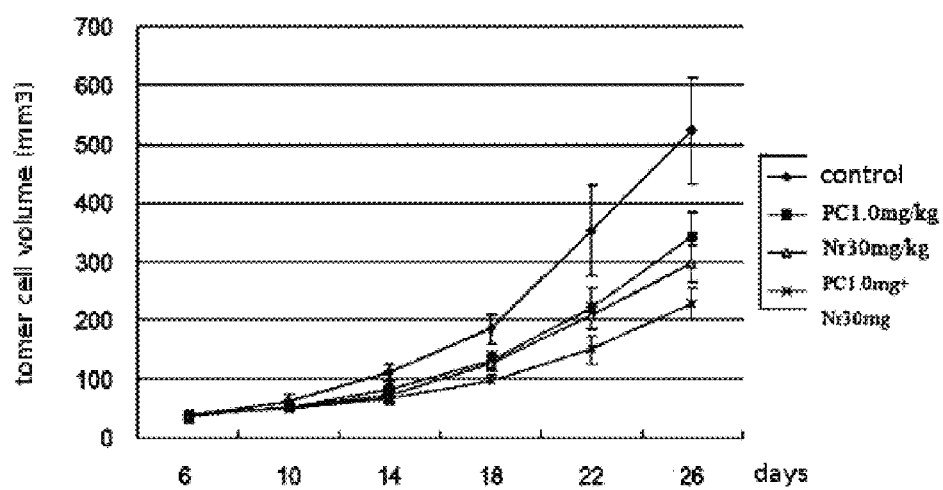
FIG. 21 shows the effect on HepG2 cell growth curve when treated with LD030 in combination with Nexavar.

A further study was conducted on liver cancer cell line in nude mice (HepG2), where Nexavar's dosage was 30 mg/kg, twice a day and LD030's dosage was 1 mg/kg, twice a day along with a blank control and a combination of LD030 and Nexavar. The result is shown in FIG. 21 where Nr stands for Nexavar. It is demonstrated that while LD030 alone has an inhibitory effect on the tumor cells, the effect is enhanced when it us used in combination with Nexavar. When compared with the blank, LD030's effect is statistically significant (p<0.05).

Table 4 shows the result of in vitro experiments which compared LD030 with SUTENT (sutent or sunitinib, by Pfizer) for their effects on the growth of HepG2 cells. The result shows that LD030 has good efficacy on inhibiting HepG2 cells and requires a lower dosage than SUTENT.

TABLE 4

In vitro effects of SUTENT and LD030 on growth of liver cancer cells

| Liver Cancer Cells | LD030 | SUTENT |
|---|---|---|
| HepG2 | IC50 = 1.33 µM | IC50 = 3.6 µM |
| HepG2 | IC50 = 1.57 µM | IC50 = 8.0 µM |

Effect of LD030 on Apoptosis of HepG2 Cells

The study was conduct by using flow cytometry to detect apoptosis of HepG2 cells after being treated for 24 hours with LD030 at concentrations 0.03 µM, 0.14 µM, 0.7 µM, 3.5 µM, and 17.5 µM along with blank control. Then proceeded as follows:

1. Collect cells ($1\text{-}5\times10^6$/mL), centrifuge at 500-1000 r/min for 5 min, and discard the culture medium.
2. Wash the cells with 3 ml PBS once.
3. Centrifuge to discard PBS, and add 70% ice-cold ethanol for fixation, 4° C., 1-2 hours.
4. Centrifuge to discard ethanol, and re-suspend in 3 ml PBS for 5 min.
5. Filter with a 400 mesh screen, and centrifuge 500-1000 r/min for 5 min to discard PBS.
6. Stain with 1 ml propidium iodide (Propidium Iodide, PI) at 4° C. in the dark for 30 min.
7. Conduct flow cytometry.

Figure 22:
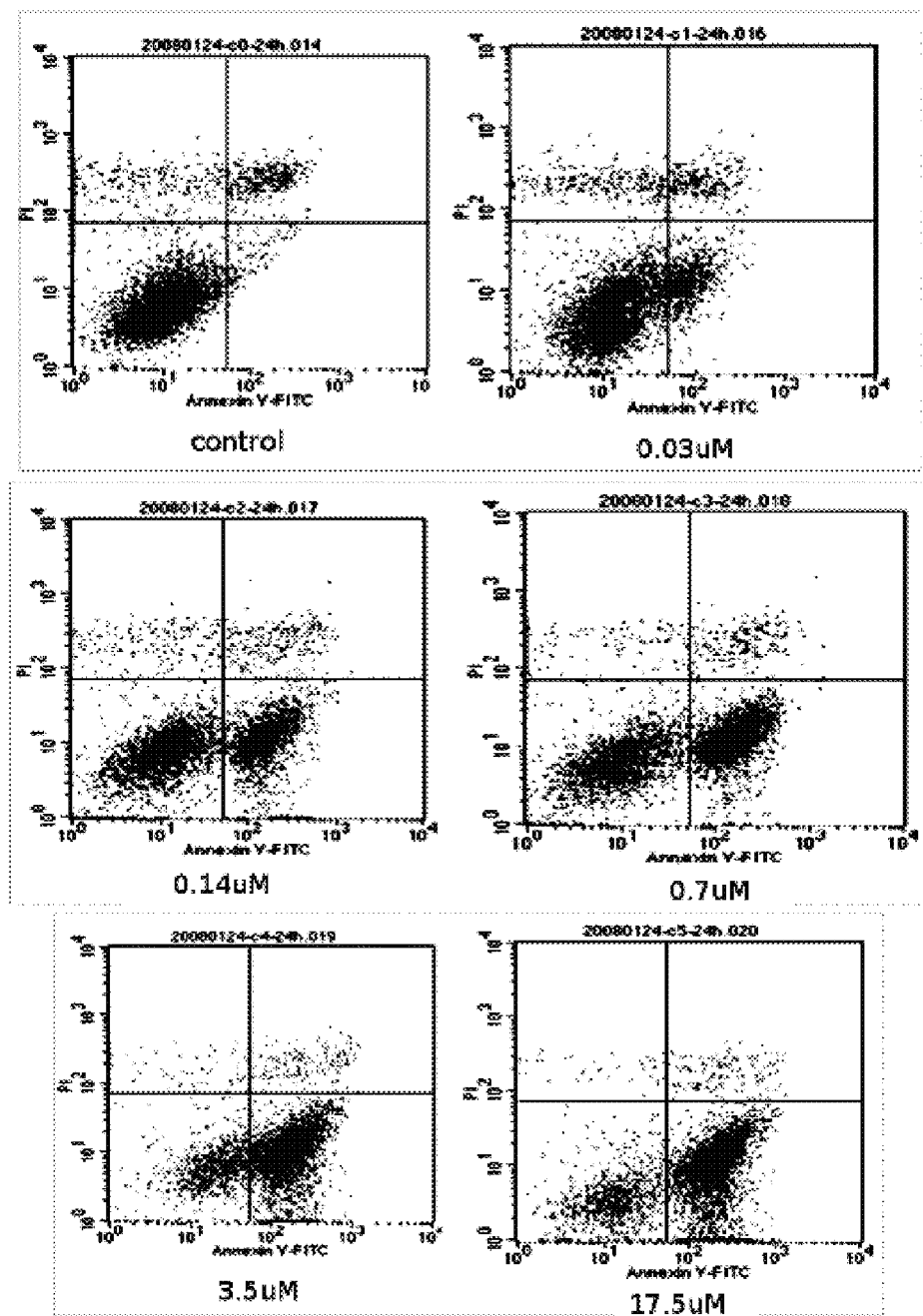
FIG. 22 shows the results of flow cytometry of HepG2 cells treated with LD030 for 24 hours.

The flow cytometry results are shown in FIG. 22 which shows the greater proportions of cell lysis with increased LD030 concentrations, indicating LD030 has inhibitory effects on HepG2 cells.

Effect of LD030 on Signal Pathway in Pancreatic Cancer Cell Line PancI

The Jak/STAT channel plays an important role in cell growth, proliferation, and survival. Using Western Blotting, the present invention studied the effect of LD030 on Jak/STAT phosphorylation in PancI cells.

The cells were treated with LD030 at concentrations of 20 µM and 50 µM, for 4 hours, 8 hours, 24 hours, and 48 hours. After the treatment, the cells were collected and subject to lysis in the buffer (50 mM Tris-HCl pH7.5, 100 mM NaCl, 5 mM EDTA, 40 mM $Na_2P_2O_7$, 1% Triton X-100, 1 mM dithiothreitol, 200 µM $Na_3VO_4$, 100 µM phenylmethysufonyl fluoride fluoride, 2 µg/ml leupeptin, 4 µg/ml aprotinin and 0.7 µg/ml pepstatin). Analysis of stained protein (Bio-Rad, 500-0006) was conduct for adjusting the protein concentration. Same quantity of protein (50 µg/lane) was used for 10% SDS-polyacrylamide gel electrophoresis, and then electrically transferred to the polyvinylidene fluoride (PVDF) membrane. The membrane was treated with antibodies specific to p-Jak2 (Cell signaling, 3771), p-Stat3 (Cell signaling, 9131) and α-tubulin (Zymed Laboratories, 32-2500). Visible protein bands were detected with an enhanced chemiluminescence (ECL Plus) detection system (Amersham).

Figure 23:
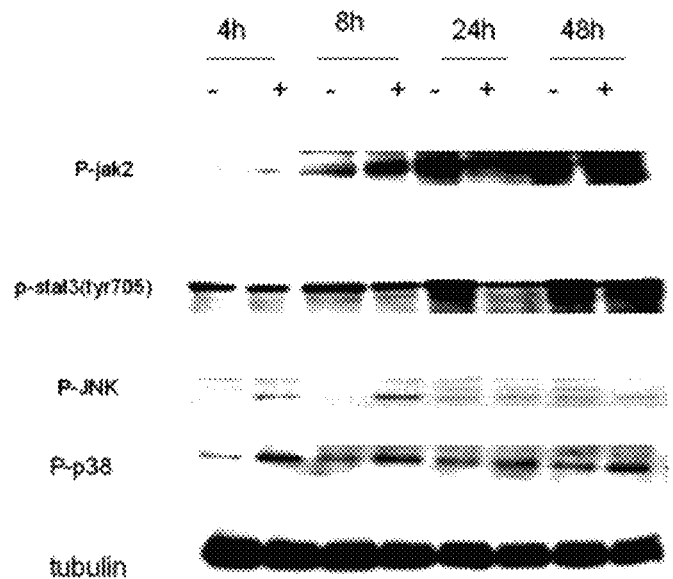
FIG. 23 shows the results of protein electrophoresis of PancI cells treated with 20 μM LD030.
Figure 24:
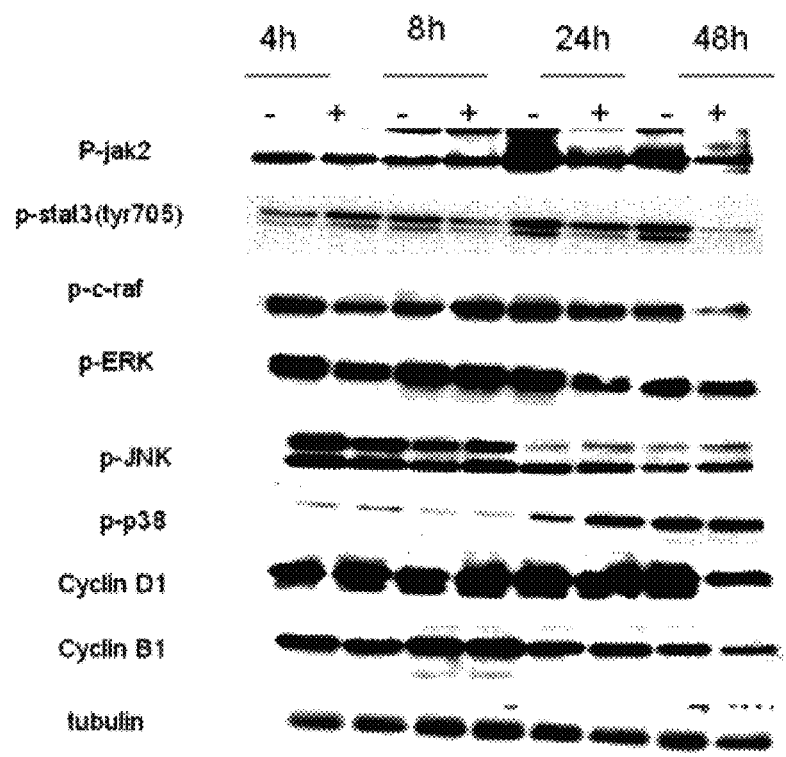
FIG. 24 shows the results of protein electrophoresis of PancI cells treated with 50 μM LD030.

The protein electrophoresis results in the above described experiments are shown FIGS. 23 and 24 for LD030 treatments at 20 µM and 50 µM, respectively. As shown in FIG. 23, where PancI cells were treated with 20 µM LD030 for 4 hours, 8 hours, 24 hours, 48 hours and p-jak2, p-stat3 (tyr705), p-JNK, P-p38 and tubulin determined by protein electrophoresis at each interval, when compared with blank control, the treatment with LD030 significantly reduced p-jak2 and p-stat3 (tyr705) at 24 hours and 48 hours, while p-p38 protein expression was increased. It is thus indicated that the LD030 treatment down-regulates Jak, Stat3-related channels, and up-regulates p-JNK and p-p38. As shown in FIG. 24, where PancI cells were treated with 50 µM LD030 for 4 hours, 8 hours, 24 hours, 48 hours, and p-jak2, p-stat3 (tyr705), pc-raf, p-ERK, p-JNK, p38, Cyclin D1, Cyclin B1 and tubulin protein determine by electrophoresis at each interval, when compared with the blank control LD030 significantly reduced p-jak2 (phosphorylated tyrosine kinase 2), p-stat3 (tyr705, phosphorylation and activation of transcription signal transduction protein 3), p-c-raf (phosphorylated proto-oncogene serine, threonine kinase) and p-ERK (extracellular signal-phosphorylation regulated kinase) at 24 hours and 48 hours, while the treatment increased the expression of p-JNK (phosphorylated c-JUN N-terminal kinase) and p-p38 (mitogen-activated protein kinase), and decreased the expression of Cyclin D1 and Cyclin B1 reduced at 48 hours. The expression of tubulin as internal reference was basically unchanged.

The above results indicate that LD030 may target the following signaling channel and proteins: (1) Jak-stat3 pathway where the target proteins are phosphorylated jak1, jak2 and stat3 (p-jak1, p-jak2, and p-stat3). (2) C-raf pathway where the target proteins are phosphorylated c-raf and ERK (pc-raf, p-ERK). (3) apoptosis pathway wherein the target proteins are phosphorylated p38 and JNK (p-p38, p-JNK).

Affinity Calculation Based on Computer Simulation of 3-D Structures

Figure 8:
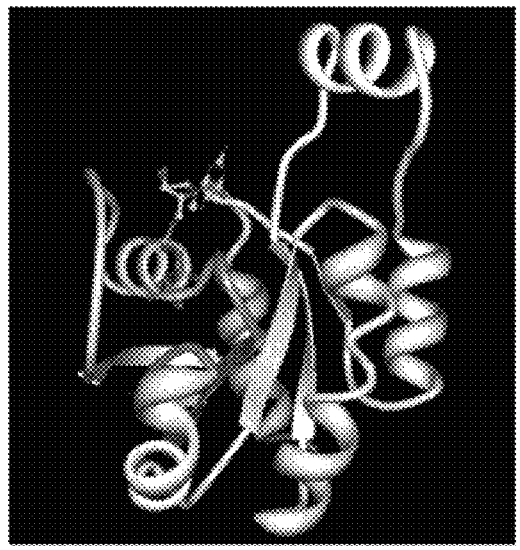
FIG. 8 shows 3-D structure of Rac-1 simulated by computer.
Figure 9:
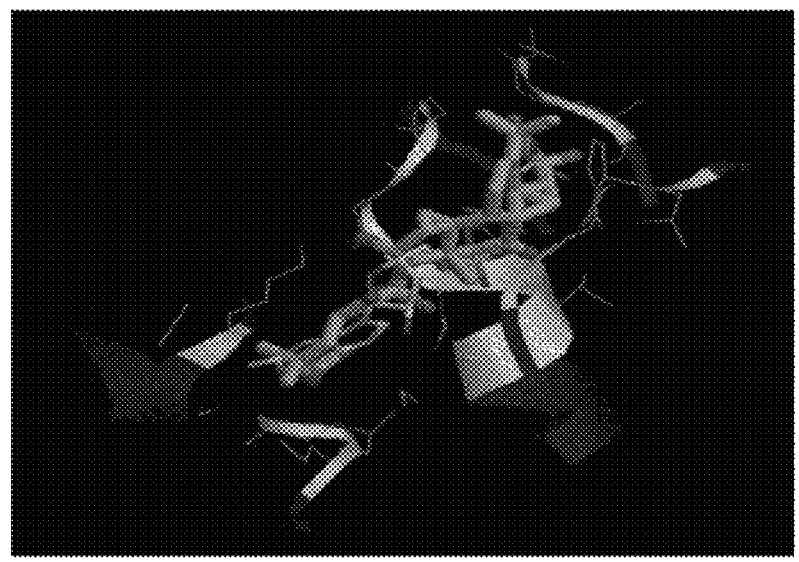
FIG. 9 shows 3-D confirmation of Rac-1 after being bound by LD030.
Figure 10:
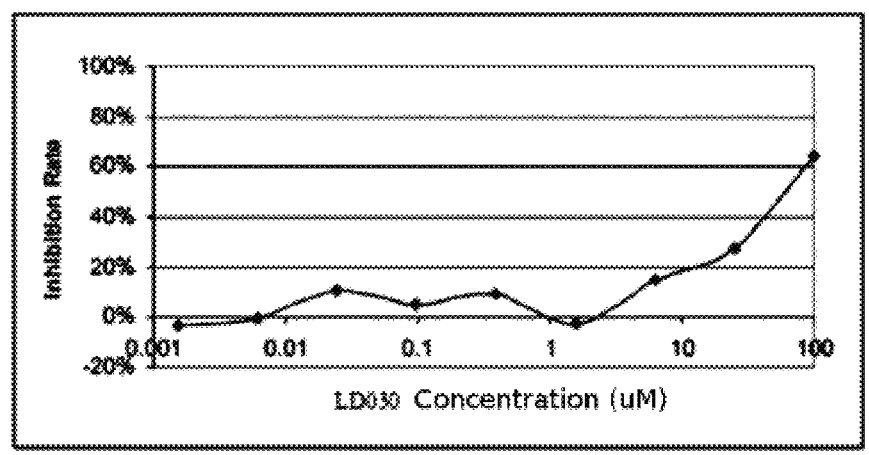
FIG. 10 shows a growth curve of HepG2 cells under the LD030 treatment.
Figure 11:
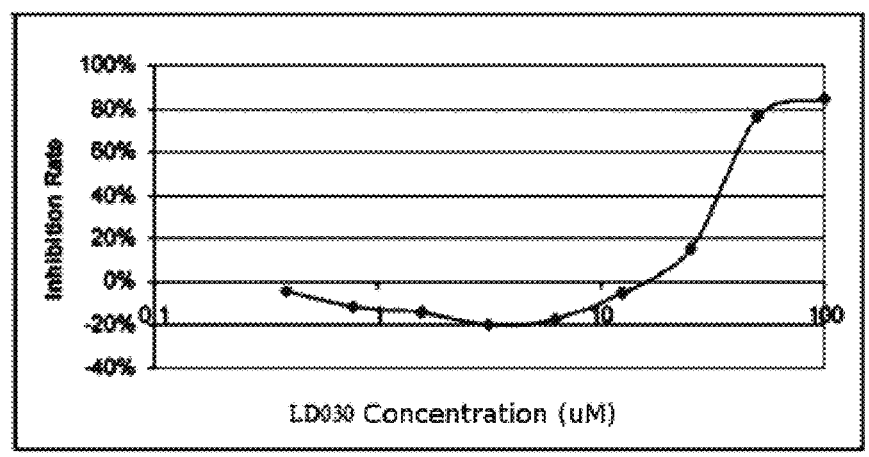
FIG. 11 shows a growth curve of PancI cells under the LD030 treatment.

The iGEMDOCK simulation software was to obtain the three-dimensional structure of Rac-1 protein which is shown in FIG. 8. The structural changes was also simulated upon binding LD030 to Rac-1 (FIG. 9) and the affinity between LD030 and Rac-1 affinity was calculated to be −146, an indication of strong binding energy. Because Rac-1 is a polyphosphate kinase in the signal transduction pathway of RHO, it suggests that LD030 may be able to block signal transduction through RHO pathway by binding to Rac-1.

Effect of Compounds Related to LD030 on Cancer Cell Lines

MTT assay was used to detect cell viability after being treated with different compounds of the present invention related to LD030. The cell lines treated were on non-small lung cancer cell line A549, HepG2 cells and Panc1 cells.

MTT preservation solution preparation: 0.5 g MTT was dissolved in 100 ml of phosphate buffer solution (PBS), and bacteria contaminates were removed with a 0.22 μm membrane filter to obtain 0.5% MTT solution, which was stored in the dark at −20° C.

MTT working solution preparation: MTT preservation solution was diluted 10 times with sterile PBS to obtain MTT working solution.

1640 complete medium preparation: 1640 base medium was added with an amount of fetal bovine serum (FBS) so that the medium contains 10% FBS by volume. Then an amount of double-antibody (i.e., penicillin and streptomycin) was added to make final concentration of penicillin at 100 units/ml and streptomycin at 100 ug/ml.

The experimental procedure is as follows:

(1) Take trypsin digested logarithmic phase cells and adjust the concentration of the cell suspension to 6×10$^4$ cell/ml, and then add 100 ul suspension of the cells under the test to each well on a 96-well plate and adjusted to a density of 6000 cells/well. The edge orifice is filled with sterile PBS.

(2) Placed the 96-well plate into a 37° C. incubator with 5% $CO_2$ and incubate it overnight.

(3) Dissolve the test compounds in 200 ul DMSO to get a 5 mg/ml solution and dilute it to get 100 uM, 10 uM, 1 uM and 0.1 uM solutions. Add 100 ul of a solution to each of three repeat wells. Set a control well which has cells but without the compound of the present invention and a blank cell which contains no cells.

(4) Put the 96-well plate into a 37° C. incubator with 5% $CO_2$ and incubate it for 48 hours. Examine the cells daily under a microscope.

(5) After being cultured for 48 hours, centrifuge and discard the culture liquid. Add 100 ul MTT working solution to each well, and continue incubating for 4 h.

(6) Terminate the culture, and carefully remove the culture medium. Then add 100 ul DMSO to each well and shake it at a low speed in a shaker for 10 min to make all crystals fully dissolved. The absorbance value of each well was measured by an enzyme-linked immunosorbent detector at the OD570 nm, and the inhibition rate of the different compounds with different concentration on cell growth can be obtained.

The growth inhibitory effects of different compounds at different concentrations on Panc1 cells, HepG2 cells and A549 cells are shown in Table 1, Tablet, and Table 3, respectively.

TABLE 1

Effects on Panc1 Cells (inhibitory percentage)

| Sample ID | The effect of different compounds with different concentrations on Panc1 cells (%) | | | |
|---|---|---|---|---|
| | 0.1 μM | 1 μM | 10 μM | 100 μM |
| LD 021 | −12.63 | −4.96 | 2.16 | 48.84 |
| LD 022 | −6.95 | −5.28 | −2.48 | −6.24 |
| LD023 | −5.92 | −1.12 | −2.56 | 25.26 |
| LD 024 | −7.19 | −8.39 | −13.03 | 6.95 |
| LD 026-2 | 8.79 | 7.59 | 14.63 | 21.50 |
| LD 028 | −9.19 | −0.48 | −0.40 | 0.16 |
| LD 012 | 5.68 | 5.68 | 10.20 | 39.54 |
| LD 014 | −5.26 | −3.05 | 3.89 | 24.08 |
| LD 025 | −16.51 | −12.83 | −9.57 | −15.98 |
| LD 026-1 | −2.84 | 9.46 | 8.83 | 34.38 |
| LD027 | 2.21 | 10.09 | 16.72 | 28.71 |

TABLE 2

Effects on HepG2 Cells (inhibitory percentage)

| Sample ID | The effect of different compounds with different concentrations on HepG2 cells (%) | | | |
|---|---|---|---|---|
| | 0.1 μM | 1 μM | 10 μM | 100 μM |
| LD 021 | 12.71 | 13.05 | 12.71 | 24.65 |
| LD 022 | 20.67 | 31.18 | 24.88 | 24.54 |
| LD 023 | 26.53 | 27.64 | 19.13 | 23.00 |
| LD 024 | 22.00 | 14.26 | 5.86 | 2.10 |
| LD 026-2 | 20.34 | 32.84 | 20.78 | 33.94 |
| LD 028 | 29.41 | 37.37 | 67.77 | 45.77 |
| LD 012 | 10.53 | −15.82 | −1.79 | 47.72 |
| LD 014 | 0.64 | −20.73 | 2.93 | 61.37 |
| LD 025 | −1.15 | −19.07 | −1.79 | 20.48 |
| LD 026-1 | −3.32 | −0.13 | 12.70 | 58.12 |

TABLE 3

Effects on A549 Cells (inhibitory percentage)

| Sample ID | The effect of different compounds with different concentrations on A549 cells (%) | | | |
|---|---|---|---|---|
| | 0.1 μM | 1 μM | 10 μM | 100 μM |
| LD 021 | 3.13 | 1.31 | 1.53 | 45.50 |
| LD 022 | 4.73 | 8.99 | 6.92 | 35.89 |
| LD 023 | 8.01 | 8.30 | 6.11 | 12.70 |
| LD 024 | 1.38 | 6.04 | −0.22 | 34.61 |
| LD 026-2 | 2.51 | 6.88 | −2.33 | 33.01 |
| LD 028 | 3.24 | 10.01 | −1.75 | 29.19 |
| LD 012 | 1.31 | 28.04 | 39.34 | 91.76 |
| LD 014 | 21.33 | 9.46 | 3.02 | 34.58 |
| LD 025 | 25.19 | 1.71 | 0.51 | 16.85 |
| LD 026-1 | 21.80 | 6.66 | 8.30 | 39.82 |
| LD 027 | −1.40 | −4.98 | 12.95 | 58.56 |

The above results indicate that at 10 μM or 100 μM, most compounds have significant effects on inhibiting cancer cells growth. Some of these compounds, such as compound LD012, have an inhibition rate more than 90% on A549.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

What is claimed is:

1. A method of treating cancer, comprising administering to a person in need of treatment the following compound:

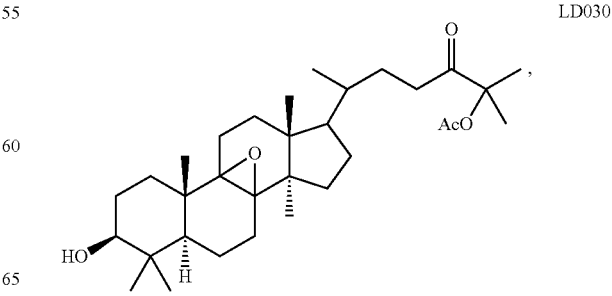

LD030 wherein said cancer is lung cancer, liver cancer, breast cancer, brain tumor or pancreatic cancer.

2. The method of claim 1, wherein said cancer is liver cancer or pancreatic cancer.

\* \* \* \* \*